US010231634B2

(12) United States Patent
Zand et al.

(10) Patent No.: US 10,231,634 B2
(45) Date of Patent: Mar. 19, 2019

(54) SURGICAL INSTRUMENTS WITH SENSORS FOR DETECTING TISSUE PROPERTIES, AND SYSTEM USING SUCH INSTRUMENTS

(71) Applicant: SURGISENSE CORPORATION, Bethesda, MD (US)

(72) Inventors: Jason Matthew Zand, Washington, DC (US); Gregory Scott Fischer, Jamaica Plain, MA (US)

(73) Assignee: SURGISENSE CORPORATION, Bethesda, MD (US)

( * ) Notice: Subject to any disclaimer, the term of this patent is extended or adjusted under 35 U.S.C. 154(b) by 0 days.

(21) Appl. No.: 14/949,846

(22) Filed: Nov. 23, 2015

(65) Prior Publication Data

US 2016/0073909 A1 Mar. 17, 2016

Related U.S. Application Data

(63) Continuation of application No. 11/918,456, filed as application No. PCT/US2006/013985 on Apr. 14, 2006, now Pat. No. 9,204,830.
(Continued)

(51) Int. Cl.
*A61B 5/1455* (2006.01)
*A61B 5/026* (2006.01)
(Continued)

(52) U.S. Cl.
CPC .......... *A61B 5/0261* (2013.01); *A61B 5/0071* (2013.01); *A61B 5/0086* (2013.01);
(Continued)

(58) Field of Classification Search
CPC .... A61B 5/0261; A61B 5/0071; A61B 5/0059
See application file for complete search history.

(56) References Cited

U.S. PATENT DOCUMENTS 4,515,165 A   5/1985   Carroll
5,318,023 A   6/1994   Vari et al.
(Continued)

FOREIGN PATENT DOCUMENTS

CN   1969773 A     5/2007
WO   98/32088 A1   7/1998
(Continued)

OTHER PUBLICATIONS

European Communication Pursuant to Article 94(3) EPC, issued in European Patent Application No. 06758332.8-2319, dated Feb. 5, 2014 (3 pages).
(Continued)

*Primary Examiner* — Eric Winakur
(74) *Attorney, Agent, or Firm* — McDermott Will & Emery LLP

(57) ABSTRACT

A system is provided that furnishes expert procedural guidance based upon patient-specific data gained from surgical instruments incorporating sensors on the instrument's working surface, one or more reference sensors placed about the patient, sensors implanted before, during or after the procedure, the patient's personal medical history, and patient status monitoring equipment. Embodiments include a system having a surgical instrument with a sensor for generating a signal indicative of a property of a subject tissue of the patient, which signal is converted into a current dataset and stored. A processor compares the current dataset with other previously stored datasets, and uses the comparison to assess a physical condition of the subject tissue and/or to guide a procedure being performed on the tissue.

16 Claims, 22 Drawing Sheets

Related U.S. Application Data

(60) Provisional application No. 60/766,359, filed on Jan. 12, 2006, provisional application No. 60/671,872, filed on Apr. 15, 2005.

(51) Int. Cl.
    *A61B 5/00* (2006.01)
    *A61B 5/145* (2006.01)
    *A61B 5/1459* (2006.01)
    *A61B 17/00* (2006.01)
    *A61B 17/068* (2006.01)

(52) U.S. Cl.
CPC .......... *A61B 5/1455* (2013.01); *A61B 5/1459* (2013.01); *A61B 5/14542* (2013.01); *A61B 5/6837* (2013.01); *A61B 5/7275* (2013.01); *A61B 5/742* (2013.01); *A61B 5/7405* (2013.01); *A61B 5/7455* (2013.01); *A61B 5/0075* (2013.01); *A61B 5/0084* (2013.01); *A61B 5/413* (2013.01); *A61B 17/068* (2013.01); *A61B 2017/00022* (2013.01); *Y10S 901/09* (2013.01); *Y10S 901/44* (2013.01)

(56) References Cited

U.S. PATENT DOCUMENTS

| | | | |
|---|---|---|---|
| 5,833,603 | A | 11/1998 | Kovacs et al. |
| 5,860,917 | A | 1/1999 | Comanor et al. |
| 5,987,346 | A | 11/1999 | Benaron et al. |
| 6,163,714 | A | 12/2000 | Stanley et al. |
| 6,173,197 | B1 * | 1/2001 | Boggett ............... A61B 5/0261 600/310 |
| 6,174,291 | B1 | 1/2001 | McMahon et al. |
| 6,317,624 | B1 | 11/2001 | Kollias et al. |
| 6,391,023 | B1 | 5/2002 | Weber et al. |
| 6,498,944 | B1 | 12/2002 | Ben-Haim et al. |
| 6,631,286 | B2 | 10/2003 | Pfeiffer et al. |
| 7,072,700 | B2 | 7/2006 | Yamamoto et al. |
| 7,139,600 | B2 | 11/2006 | Maki et al. |
| 7,311,661 | B2 | 12/2007 | Heinrich |
| 7,322,971 | B2 | 1/2008 | Shehada |
| 7,341,557 | B2 | 3/2008 | Cline et al. |
| 7,364,574 | B2 | 4/2008 | Flower |
| 7,420,151 | B2 | 9/2008 | Fengler et al. |
| 7,640,046 | B2 | 12/2009 | Pastore et al. |
| 7,720,521 | B2 | 5/2010 | Chang et al. |
| 7,720,532 | B2 | 5/2010 | Hashimshony et al. |
| 7,722,534 | B2 | 5/2010 | Cline et al. |
| 7,769,432 | B2 | 8/2010 | Klimberg et al. |
| 7,918,559 | B2 | 4/2011 | Tesar |
| 7,979,107 | B2 | 7/2011 | Lin et al. |
| 8,185,176 | B2 | 5/2012 | Mangat et al. |
| 8,630,698 | B2 | 1/2014 | Fengler et al. |
| 8,647,605 | B2 | 2/2014 | Mangat et al. |
| 8,961,403 | B2 | 2/2015 | Cline et al. |
| 9,204,830 | B2 | 12/2015 | Zand et al. |
| 2003/0088162 | A1 | 5/2003 | Yamamoto et al. |
| 2006/0239921 | A1 | 10/2006 | Mangat et al. |
| 2007/0208252 | A1 | 9/2007 | Makower |
| 2008/0221648 | A1 | 9/2008 | Flower |
| 2008/0228037 | A1 | 9/2008 | Cline et al. |
| 2008/0291397 | A1 | 11/2008 | Tesar |
| 2009/0203994 | A1 | 8/2009 | Mangat et al. |
| 2009/0259107 | A1 | 10/2009 | Crenshaw et al. |
| 2009/0303317 | A1 | 12/2009 | Tesar |
| 2010/0198010 | A1 | 8/2010 | Cline et al. |
| 2010/0210904 | A1 | 8/2010 | Cline et al. |
| 2010/0222673 | A1 | 9/2010 | Mangat et al. |
| 2014/0194687 | A1 | 7/2014 | Fengler et al. |
| 2014/0308210 | A1 | 10/2014 | Mangat et al. |

FOREIGN PATENT DOCUMENTS

| | | |
|---|---|---|
| WO | 00/018294 A1 | 4/2000 |
| WO | 02/07617 A2 | 1/2002 |
| WO | 03/090630 A2 | 11/2003 |
| WO | 2006113394 A3 | 4/2009 |

OTHER PUBLICATIONS

European Communication Pursuant to Article 94(3) EPC, issued in European Patent Application No. 06758332.8-2319, dated Dec. 5, 2012; 5 pages.
Canadian Office Action and Examinatin Search Report issued in corresponding Canandian Patent Application No. 2,604,563, dated Oct. 24, 2014; 5 pages.
Chinese Notiification of First Office Action issued in corresponding Chinese Patent Application No. 200680021505.X, dated Sep. 14, 2010; 16 pages with English translation.
Chinese Notification of Third Office Action issued in corresponding Chinese Patent Application No. 200680021505.X, dated Sep. 7, 2012; 6 pages with English translation.
Chinese Notification of Fourth Office Action issued in corresponding Chinese Patent Application No. 200680021505.X, dated Feb. 8, 2013; 24 pages with English translation.
Chinese Notice of Allowance, issued in corresponding Chinese Patent Application No. 2006800021505.X, dated May 16, 2013; 4 pages with English translation.
Chinese Notification of First Office Action issued in corresponding Chinese Patent Application No. 201310328574.7, dated Mar. 27, 2015; 11 pages with English translation.
Product Description: SPY Elite: SPY Imaging for Open Surgery, available in novadaq.com. Retrieved on Apr. 24, 2015 at http:/fnovadaq.com/products/spy-elite; 1 page.
Product Description: PINPOINT Endoscopic Fluorescence Imaging: PINPOINT Imaging for Minimally Invasive Surgery, available in novadaq.com. Retrieved on Apr. 24, 2015 at http:/fnovadaq.com/products/pinpoint-endoscopic-fluorescence-imaging; 2 pages.
Company Description: Technologies and Intellectual Property: SPY Imaging Technology, available in novadaq.com. Retrieved on Apr. 24, 2015 at http:/fnovadaq.com/company/technologies-ip.
European Search Report issued in European Patent Application No. 06758332.8-2319, dated Sep. 21, 2010.
Chinese Office Action, w/ English translation thereof, issued in Chinese Patent Application No. 200680021505.X, dated Dec. 19, 2011.
International Preliminary Report on Patentability issued in corresponding International Application No. PCT/US06/13985, dated Dec. 7, 2007.
Non-Final Office Action issued in related U.S. Appl. No. 11/918,456, dated Mar. 6, 2012.
Final Office Action issued in related U.S. Appl. No. 11/918,456, dated Dec. 12, 2012.
Non-Final Office Action issued in related U.S. Appl. No. 11/918,456, dated May 9, 2014.
Non-Final Office Action issued in related U.S. Appl. No. 11/918,456, dated Dec. 2, 2014.
Notice of Allowance issued in related U.S. Appl. No. 11/918,456, dated Jul. 31, 2015.
Notification of Second Chinese Office Action dated Jan. 6, 2016, issue din corresponding Chinese Application No. 201310328574.7. (w/ English translation).
Extended European Search Report dated Sep. 5, 2016, issued in European Patent Application No. 16001279.5.
Chinese Office Action dated Sep. 28, 2016, issued in Chinese Patent Application No. 201310328574.7 (w/ English translation).
Canadian Office Action dated Feb. 22, 2017, issued in Canadian Patent Application No. 2,604,563.
Chinese Office Action dated May 2, 2017, issued in Chinese Application No. 201310328574.7 (w/ English translation).
Office Action issued in Canadian Patent Application No. 2,604,563, dated Feb. 23, 2018.

(56) References Cited

OTHER PUBLICATIONS

Supplementary European Search Report for European Patent Application No. 06 75 8332, dated Sep. 13, 2010.

* cited by examiner

Section A-A

SURGICAL INSTRUMENTS WITH SENSORS FOR DETECTING TISSUE PROPERTIES, AND SYSTEM USING SUCH INSTRUMENTS

RELATED APPLICATIONS

This application is a continuation of U.S. patent application Ser. No. 11/918,456, filed on Oct. 15, 2007, which is a U.S. National Phase under 35 U.S.C. § 371 of International Patent Application No. PCT/US2006/013985, filed on Apr. 14, 2006, which in turn claims the benefit of U.S. Provisional Application No. 60/766,359, filed on Jan. 12, 2006 and U.S. Provisional Application No. 60/671,872, filed on Apr. 15, 2005, the disclosures of which Applications are incorporated by reference herein.

FIELD OF THE INVENTION

The present invention relates to surgical instruments, specifically to surgical instruments with sensors used to detect properties of biological tissue, and a system for exploiting the information gathered by the sensors.

BACKGROUND ART

A living organism is made up of cells. Cells are the smallest structures capable of maintaining life and reproducing. Cells have differing structures to perform different tasks. A tissue is an organization of a great many similar cells with varying amounts and kinds of nonliving, intercellular substances between them. An organ is an organization of several different kinds of tissues so arranged that together they can perform a special function.

Surgery is defined as a branch of medicine concerned with diseases requiring operative procedures.

Although many surgical procedures are successful, there is always a chance of failure. Depending on the type of procedure these failures can result in pain, need for re-operation, extreme sickness, or death. At present there is no reliable method of predicting when a failure will occur. Most often the failure occurs after the surgical procedure has been completed. Failures of surgical procedures can take many forms. The most difficult failures to predict and avoid are those that involve biological tissue. This difficulty arises for three distinct reasons. Firstly, the properties that favor the continued function of biological tissue are very complex. Secondly, these properties are necessarily disrupted by surgical manipulation. Finally, the properties of biological tissues vary between people.

During a surgical operation, a variety of surgical instruments are used to manipulate biological tissues. However, traditional surgical instruments do not have the ability to obtain information from biological tissues. Obtaining information from the biological tissues that surgical instruments manipulate can provide a valuable dataset that at present is not collected. For example, this dataset can quantitatively distinguish properties of tissues that will result in success or failure when adapted to specific patient characteristics.

Surgical instruments that incorporate sensors onto the instruments' working surfaces are described, e.g., in U.S. patent application Ser. No. 10/510,940 and in U.S. Pat. No. 5,769,791. The instruments described in the prior art have the ability to sense tissue properties; however, their utility is limited by an inability to account for the multitude of differences that exist between patients. This limitation of the prior art is clearly illustrated by the fact that the instruments generate feedback after sensor signals are compared to a fixed dataset within the device. Thus, the prior art instruments have no means of adapting to patient-specific characteristics that are of utmost importance in avoiding surgical procedure failure.

There exists a need for a system and methodology for using the information gathered by surgical instruments having sensors in an adaptive, patient-specific manner. There also exists a need for instruments having sensors that are useful for monitoring a patient's condition during and after surgery.

SUMMARY OF THE INVENTION

An advantage of the present invention is a system which generates real time, patient specific procedural guidance for predicting success of a surgical procedure, and avoiding or detecting failure of the procedure. Another advantage of the present invention is a system which records data across the entire patient encounter including pre-operative, intra-operative and post-operative periods, as well as immediate, acute, short term, and long term outcomes both locally in hospital-based units as well as remotely in a data repository.

A further advantage of the present invention is a system which provides expert procedural guidance based upon patient specific data gained from personal medical history, patient status monitoring equipment, surgical instruments incorporating sensors on the instrument's working surface, reference sensors placed about the patient, and implanted sensors placed before, during or after the procedure.

A still further advantage of the present invention is a system which generates patient specific expert guidance in optimizing surgical procedures based upon statistically matched data from a central repository. Yet another advantage of the present invention is a system which adapts its guidance based on continuously updated, statistically significant data.

According to the present invention, the foregoing and other advantages are achieved in part by a system comprising a surgical instrument having a sensor for generating a signal indicative of a property of a subject tissue of a patient; a signal processor for receiving the signal and converting the signal into a current dataset; a memory for storing the current dataset; and a processor. The processor is configured to compare the current dataset with other datasets previously stored in the memory, and to assess a physical condition of the subject tissue or guide a current procedure being performed on the tissue, responsive to the comparison.

Another aspect of the present invention is a system comprising a surgical instrument comprising an incident light source and a sensor for using incident light from the light source to generate a signal indicative of fluorescence of a subject tissue into which a fluorescent medium has been introduced; and a processor configured to receive the signal and to determine a tissue characteristic of the subject tissue responsive to the response of the fluorescence as indicated by the signal.

A further aspect of the present invention is a sensor consisting essentially of a rigid or flexible substrate and a plurality of sensing elements mounted to the substrate for monitoring a property of a living tissue.

A still further aspect of the present invention is a surgical fastening device comprising a sensor for measuring properties of and interaction with a living tissue on the fastening device.

A further aspect of the present invention is a system comprising a surgical instrument having a sensor for generating a signal indicative of a property of a subject tissue of a patient; a reference measurement instrument having a sensor for measuring a reference tissue and generating a reference measurement signal; a signal processor for receiving the signal and converting the signal into a current dataset, and for receiving the reference measurement signal and converting it into a current reference dataset; a memory for storing the current dataset and the current reference dataset; and a processor. The processor is configured to compare the current dataset with the current reference dataset, and to assess a physical condition of the subject tissue and/or guide a current procedure being performed on the tissue, responsive to the comparison.

Another aspect of the present invention is a system for monitoring a living tissue of a patient's body, comprising a sensor implantable in the patient's body for generating a signal indicative of a property of the tissue; a controller for receiving the signal outside the patient's body; and a communications interface for communicating the signal from the sensor to the controller.

Additional advantages of the present invention will become readily apparent to those skilled in this art from the following detailed description, wherein only selected embodiments of the present invention are shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein:

FIG. 12b is a cross-sectional view the sensing staple or clip of FIG. 12a.

DESCRIPTION OF THE INVENTION

Conventional surgical instruments having sensors for measuring tissue properties have no means of adapting to patient-specific characteristics that are of utmost importance in avoiding surgical procedure failure. The present invention addresses and solves these problems stemming from conventional sensing surgical instruments.

According to the present invention, a system provides expert procedural guidance based upon patient specific data gained from surgical instruments incorporating sensors on the instrument's working surface, one or more reference sensors placed about the patient, sensors implanted before, during or after the procedure, the patient's personal medical history, and patient status monitoring equipment. In certain embodiments, the system records data across the entire patient encounter including pre-operative, intra-operative and post-operative periods, as well as immediate, acute, short term, and long term outcomes both locally in hospital-based units as well as remotely in a data repository.

In other embodiments, the inventive system generates patient-specific expert guidance in optimizing surgical procedures based upon statistically matched data from a central repository, and/or adapts its guidance based on continuously updated, statistically significant data.

The present invention will now be described in detail with reference to FIGS. 1-14.

Figure 1:
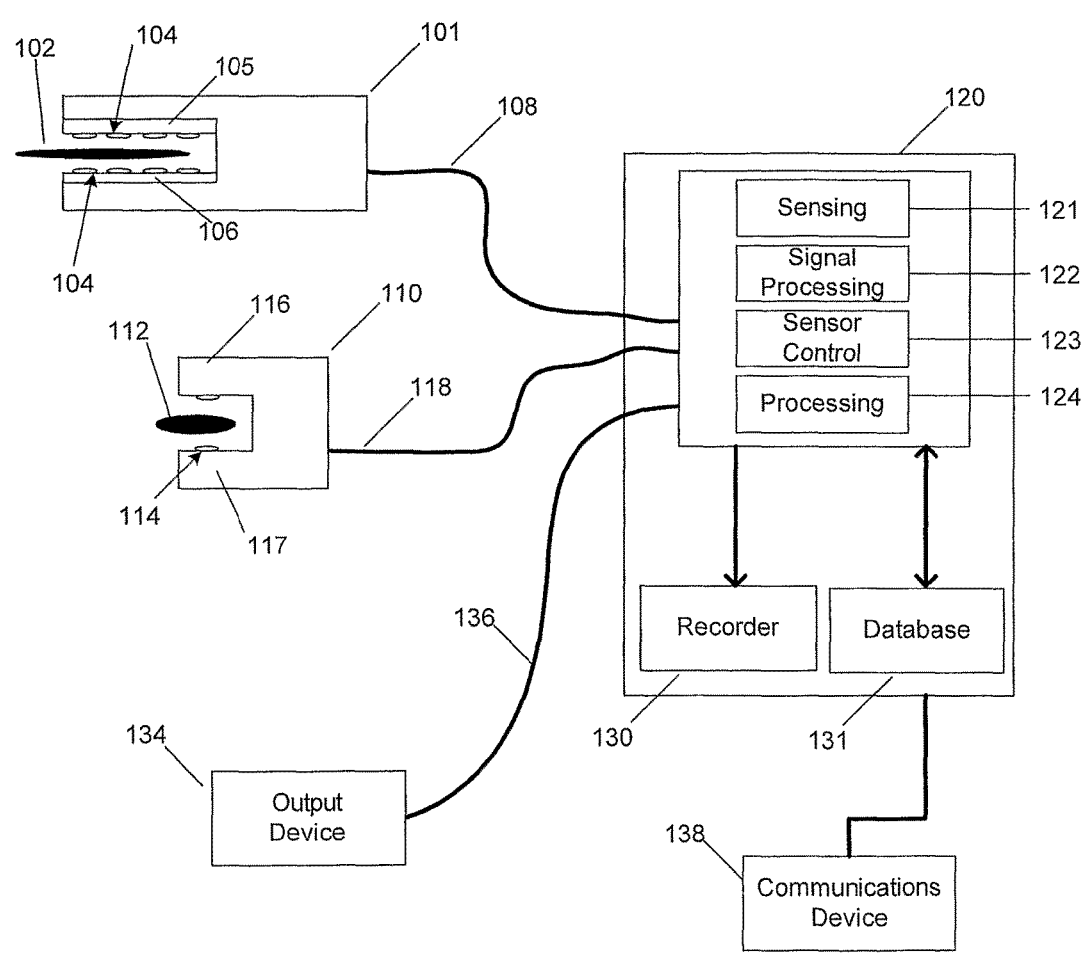
FIG. 1 is a block diagram of a sensing surgical instrument system according to an embodiment of the present invention.

FIG. 1 schematically shows a representative sensing surgical instrument system with adaptively updating algorithms according to an embodiment of the present invention. This embodiment specifically depicts a sensing surgical stapler 101 for measuring properties of tissue 102. One or more other similarly instrumented well-known surgical instruments including, but not limited to, clip appliers, graspers, retractors, scalpels, forceps, electrocautery tools, scissors, clamps, needles, catheters, trochars, laparoscopic tools, open surgical tools and robotic instruments may be integrated into the system instead of or in addition to stapler 101. Sensing elements 104 reside on the stapling element side 105 and/or the anvil side 106. The stapler is coupled via a conventional optical, electrical, or wireless connection 108 to a processing and control unit 120.

The system of FIG. 1 includes one or more reference measurement points, internal or external, invasive, minimally invasive or noninvasive, intracorporeal or extracorporeal. One example of such a reference measurement sensor, shown in the form of a clip 110, grasps reference tissue 112, typically healthy tissue in the same patient serving as a reference for use as a patient-specific baseline measurement. Sensing elements 111 are on one or both sides of the jaws 116 and 117. Reference sensor 110 need not be a clip, but can be a probe or any other sensing instrument or device. Reference sensor 110 is coupled via a conventional optical, electrical, or wireless connection 118 to processing and control unit 120.

In certain embodiments of the inventive system of FIG. 1, optical signals are generated by the sensor controller 123, light returning from the distal end of the sensors is received by sensing unit 121, and the associated signals are conditioned in signal processor 122 and converted into a dataset, which is stored in a memory, such as database 131. A processor 124, is coupled to both the input and output datasets and compares the information to determine characteristics of the tissue, the patient, and the procedure. The processor 124 comprises, for example, a conventional personal computer or an embedded microcontroller or microprocessor. Control and monitoring of the sensor outputs 123 and inputs 121 respectively is performed with conventional commercially available or custom-made data acquisition hardware that is controlled by the processor 124. Signal processor 122 is integral with processor 124, or is a conventional digital or analog signal processor placed between the sensor input 121 and the processor 124. Depending on the sensing modality, the sensor data is translated into information that relates to tissue properties. In one exemplary optical sensing embodiment, oximetry-type techniques are used to convert the relative absorption of different wavelengths of light into an oxygen saturation percentage of hemoglobin in the blood. In another optical sensing modality, fluorescence response due to a fluorescent medium that has been introduced into the body is measured, and characteristics of the response including the intensity rise time and steady state value are indicative of the blood flow in the tissue in question. All raw data and processed results are recorded by a recorder 130. This dataset can include measurements made preoperatively, intra operatively, and/or post operatively, as well as pre procedurally (before actuation of the device), at the time of the procedure (as the device is actuated), and/or post procedurally (immediately and delayed after actuation of the device). In addition, outcomes are recorded; these outcomes include immediate outcomes (during procedure), acute outcomes (within 24 hours), short term outcomes (within 30 days), and long term outcomes. Post procedure outcomes can be either quantitative measurements from implantable or other sensors, lab results, follow up imaging or other sources, or they can be qualitative assessments of the patient and the procedure by a medical professional.

A dynamically updated database of past patient encounters 131 is coupled with the processor 124 for creating a decision about tissue health based on previous knowledge. Database 131 includes information about the current patient and also data from previous patients that is used to make an informed decision about the tissue health and the likelihood of success of a procedure. The system offers solutions to the medical team to optimize the chance of procedural success. The collected dataset including sensor data and outcomes from the current procedure are added to database 131 to help make more informed future decisions. Outcomes can be added, after follow up visits with the patient at a later date, into either the system or a external database from an external source. The database 131 may be stored locally in base unit 120 or externally, but is updated by and sends updates to a central database that serves other base units 120 via a communications device 138, such as a conventional modem, an internet connection, or other network connection. Further, recorder 130 can be linked to a central repository for patient information to include some or all recorded information with medical history in patient records.

Large amounts of data are collected for each patient. The database 131 contains all of the collected information and the corresponding outcomes, or a statistically significant subset of the collected data and patient outcomes. The database, or a subset thereof, acts as a statistical atlas of predicted outcomes for a given set of sensor inputs. Conventional techniques are used for determining the relationship between the current sensor readings and those of the atlas, to interpolate or extrapolate a predicted outcome or likelihood of procedure success or failure. One technique well-known in the art represents the current patient's sensor and other inputs in a vector; the similar datasets from the atlas or database are represented in a similar form as a set of vectors. The "distance" between the current patient data and each set of previously stored data is determined; distance can be determined as the standard Euclidean distance between the vectors; i.e. the 2-norm of the difference between the vectors, or other distance measures as known in the art including other norms and the Mahalanobis distance. The difference between the vectors, or the vectors themselves, can be multiplied by a weighting matrix to take into account the differences in the significance of certain variables and sensor readings in determining the outcome. The set of distances of the current dataset from the previously stored sets is used as a weighting factor for interpolating or extrapolating the outcome, likelihood of success or failure, or other characteristics of the previously stored datasets. In another well-known technique, methods typically used in image processing and statistical shape modeling for deforming a statistical atlas can be incorporated. A base dataset generated from the database of previously collected datasets and the most statistically significant modes of deformation are determined, where the previously collected datasets act as training datasets. The magnitudes of the deformation for each mode are determined to best match the atlas model to the current dataset. The magnitudes are then used to deform the set of previous outcomes in a similar fashion, or otherwise interpolate between the previous outcomes by determining how the each outcome is dependent on each mode of deformation, to determine the best fit for the current patient. Other conventional techniques for predicting outcomes based on prior and current datasets are based on determining the similarity between the current dataset with those that were previously acquired from other patients, and using the similarity measure to determine a likelihood of a given outcome responsive to those corresponding to the prior datasets.

Attached to, or integrated directly into, the base control unit 120 is one or more output devices 134. Output device 134 is used to provide persons performing the procedure information about the physiologic condition of the tissue, and to help guide the procedure. The output device 134 takes information from the sensors, prior data, patient records, other equipment, calculations and assessments, and other information and presents it to the clinician and operating room staff in a useful manner. In one embodiment, the measured information is compared with prior datasets and prior patient outcomes, and the output device displays information to help assess the likelihood of success of a given procedure with the current configuration. The information displayed can simply be a message such as "go ahead as planned" or "choose another site." In another embodiment, the information is encoded in some form of sensory substitution where feedback is provided via forms including, but not limited to, visual, audible, or tactile sensation.

Figure 2A:
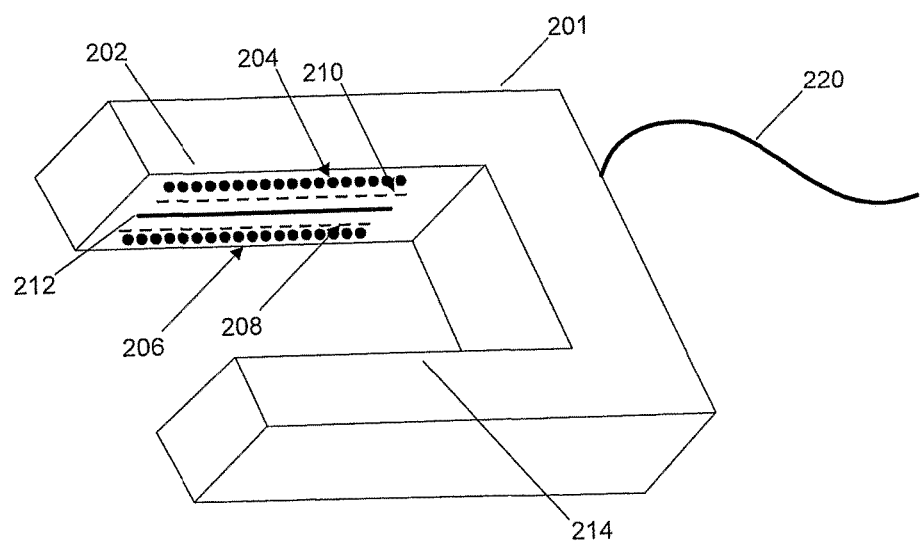
FIG. 2a shows a right angle surgical stapler according to an embodiment of the present invention.
Figure 2B:
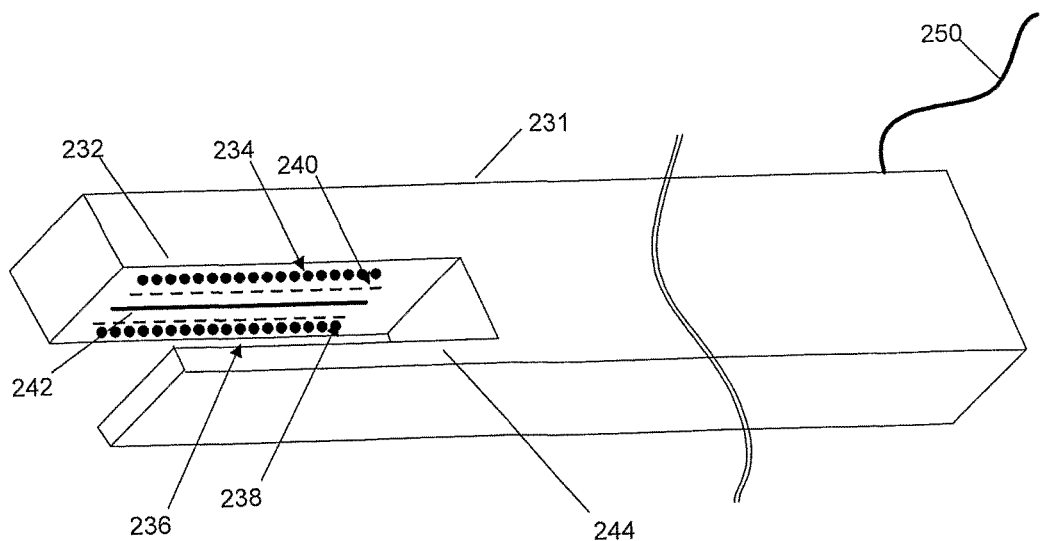
FIG. 2b shows a linear surgical stapler according to an embodiment of the present invention.
Figure 2C:
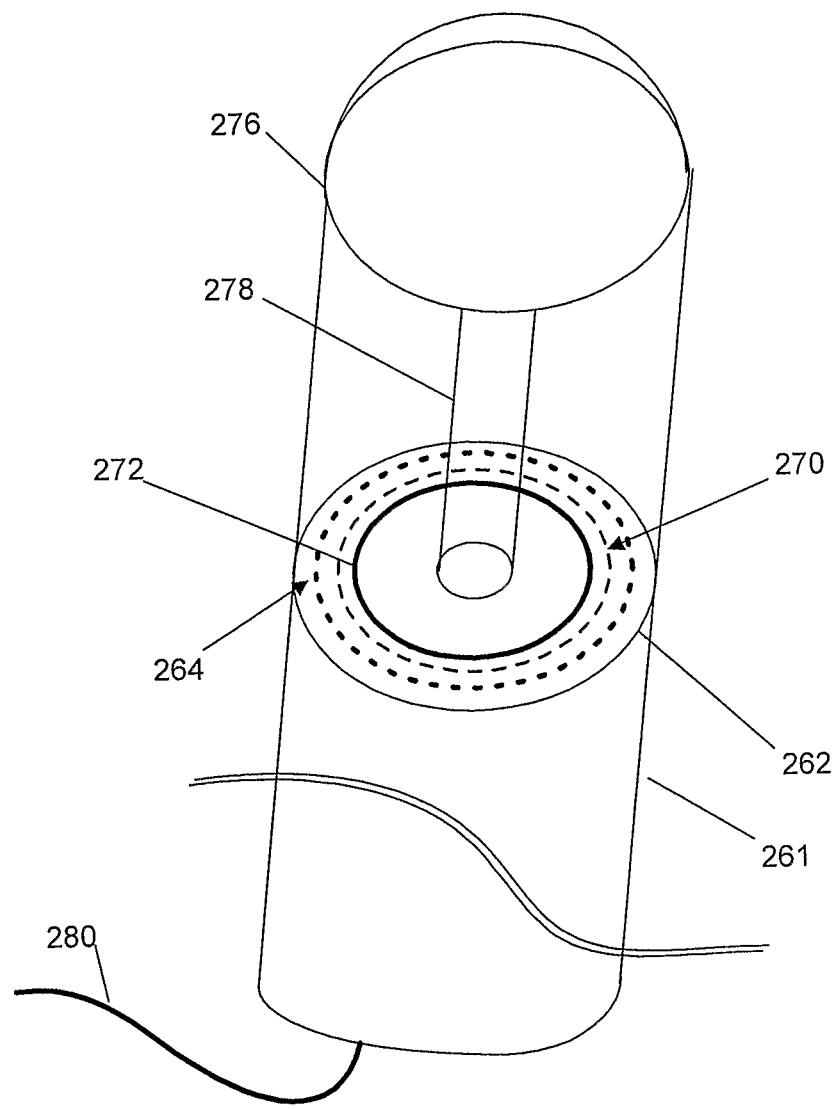
FIG. 2c shows a circular surgical stapler according to an embodiment of the present invention.

FIGS. 2*a*-2*c* depict specific stapler configurations according to embodiments of the present invention. FIG. 2*a* depicts a right angle surgical stapler 201. The stapling element side of the jaws 202 is instrumented with sensing elements 204 and 206 associated with each set of staple lines 208 and 210 which are on both sides of the cutter 212. In this embodiment, the anvil side of the jaws 214 is not instrumented with sensors. Sensing elements 204 and 206 can be placed on either or both sides of the jaws 202 and 214. In one embodiment, the stapler is coupled via optical cable 220 to the previously described processing and control unit 120. This coupling 220 can also be electrical or wireless.

FIG. 2*b* depicts a linear surgical stapler 231 according to an embodiment of the present invention. The stapling element side of the jaws 232 is instrumented with sensing elements 234 and 236 associated with each set of staple lines 238 and 240 which are on both sides of the cutter 212. In this embodiment, the anvil side of the jaws 214 is not instrumented with sensors. Sensing elements 204 and 206 can be placed on either or both sides of the jaws 232 and 234. The stapler is coupled via optical cable 250 to the previously described processing and control unit 120. This coupling 250 is electrical or wireless.

FIG. 2*c* depicts a circular surgical stapler 261 according to an embodiment of the present invention. The stapling element side of the jaws 262 is instrumented with a ring of sensing elements 264 associated the ring of staples lines 270 and outside of the circular cutter 272. Since the anvil is detachable and connected by pin 278, in this embodiment, the anvil side of the stapler 276 is not instrumented with sensors. Sensing elements 264 are placed on either or both the stapling element side 264 and the anvil side 276. The stapler is coupled via optical cable 280 to the previously described processing and control unit 120. Alternatively, this coupling 280 is electrical or wireless. Other stapler designs or clip appliers are instrumented similarly, with one or more sensors on one or both sides of the jaws.

Figure 3A:
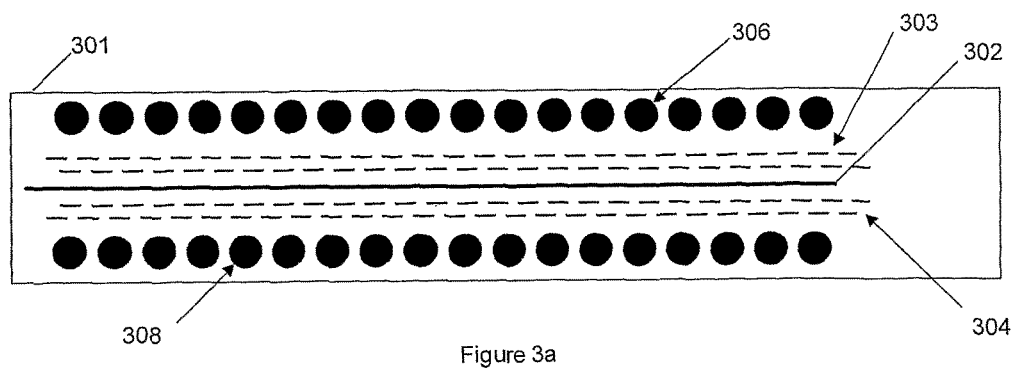
FIG. 3a shows sensing elements situated on a staple side outside of the staple lines of a surgical stapler according to an embodiment of the present invention.
Figure 3B:
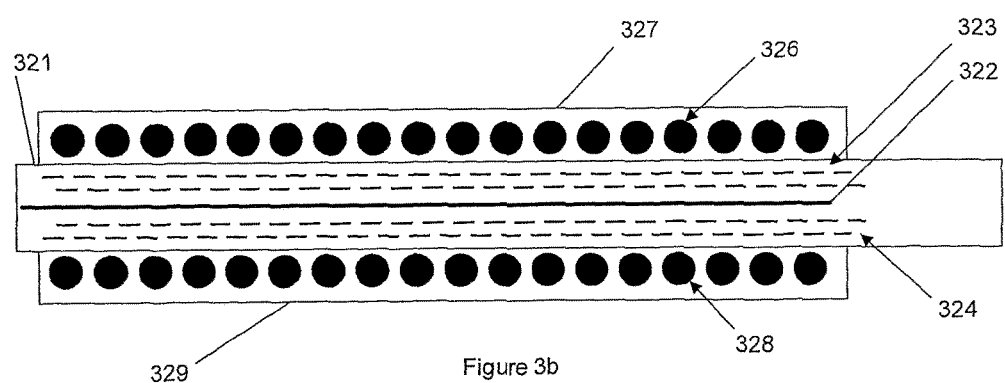
FIG. 3b shows sensing elements situated in a sleeve fixed to a stapler head of a surgical stapler according to an embodiment of the present invention.
Figure 3C:
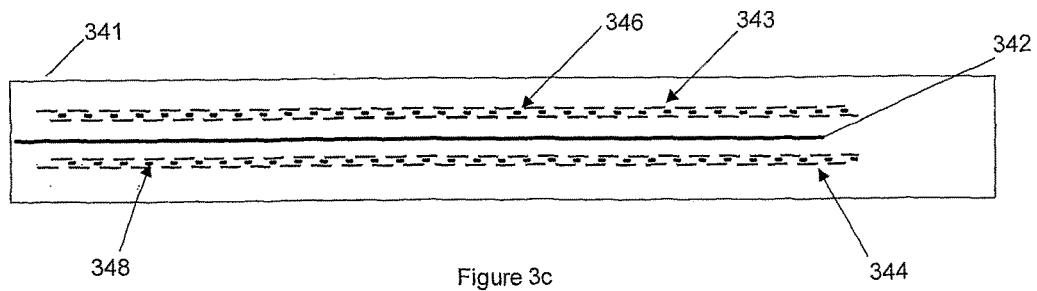
FIG. 3c shows sensing elements interleaved with staples in a surgical stapler according to an embodiment of the present invention.

FIGS. 3*a*-3*c* show configurations of sensing elements on the surface of a linear stapler according to embodiments of the present invention. These configurations are generalized to any shaped stapler or other surgical instrument. Sensing elements are shown in a linear arrangement; they can be arranged in other patterns including staggered rows, randomized, single sensors and arrays of sensors. FIG. 3*a* shows a linear stapler head 301 with sensing elements 306 and 308 on the outside of staple or clips 303 and 304, which are outside the cutter 302. Cutter 302 is optional, and there may be a total of one or more staples, staple lines, or clips. The sensing elements 306 and 308 are situated such that they sense the tissue outside of the staple lines on one or both sides.

FIG. 3*b* shows a linear stapler head 321 according to an embodiment of the present invention. Attached to the stapler or integrated into stapler head 321 is a strip or shell 327 and 329. This shell can be permanently integrated into the stapler or an addition to the stapler. Thus, it can be a modification to an existing stapler. Enclosed in the sensing shell 327, 329 are sensing elements 326 and 328. The stapler comprises one or more staples or clips 323 and 324 and cutters 322.

FIG. 3*c* shows a linear stapler head 341 with the sensing elements 346 and 348 integrated into the stapler head, according to an embodiment of the present invention. The sensing elements are placed such that they are in line with or integrated between the staples or clips 343, 344. Medial to the staples and sensors is an optional cutter 342. The sensors are placed on one or both sides of the cutter.

FIGS. 4*a*-4*e* show configurations of optical sensing elements according to embodiments of the present invention where a surgical instrument is coupled to base unit 120 optically. This coupling can also be electrical or wireless with the actual electronic sensing elements placed in the instrument as opposed to an optical coupling from a remote source.

Figure 4A:
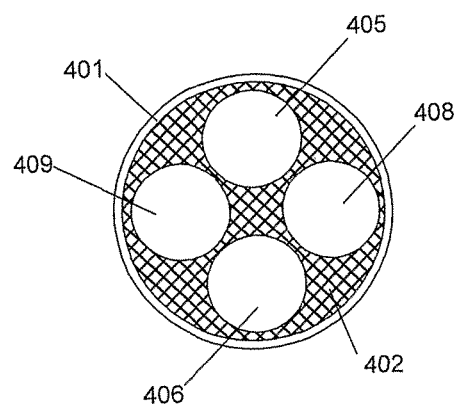
FIGS. 4a-4e show fiber configurations of an optical sensor tip according to embodiments of the present invention.

FIG. 4*a* shows an embodiment where the sensing element contains four optical fibers 405, 406, 408, and 409. These are embedded in a medium 402, typically optical epoxy, and enclosed in sheath or ferrule 401. In this embodiment, two optical fibers are used to transmit light into the tissue and two others are used to return light to the receiver in the base unit 120. The arrangement of the emitting and receiving elements is such that matching emitter/receiver pairs are adjacent or opposing. Further, the same optical fiber can be used to transmit light in both directions. One or more optical fibers are used to transmit light to and from the working surface of the instrument.

Figure 4B:
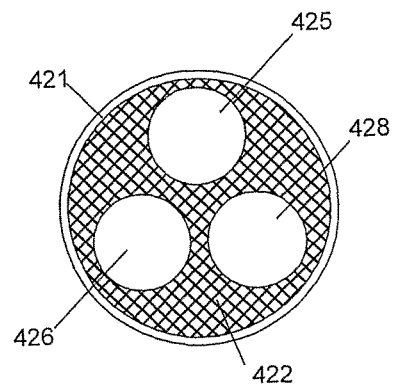
Figure 4C:
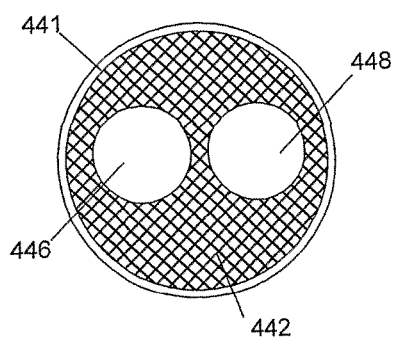

FIG. 4*b* shows an optical fiber arrangement with fibers 425, 426, and 428 embedded in a medium 422 which is enclosed in a sheath or ferrule 421. In this embodiment of the invention, two optical fibers are used for transmitting light into the tissue and a single fiber is used to return light to the receiver. FIG. 4*c* shows a similar embodiment where there are two optical fibers 446 and 448 embedded in medium 442 inside of sheath or ferrule 441. In this embodiment, a single optical fiber transmits all light to the tissue and a single fiber receives light from the tissue.

Figure 4D:
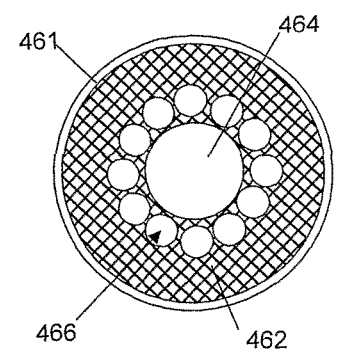

FIG. 4d shows an embodiment where there is a ring of optical fibers 466 that surround optical fiber 464 inside of medium 462 enclosed in sheath or ferrule 461. The outer ring of fibers 466 is used to transmit light while the inner fiber 464 receives light. Alternatively, the outer ring of fibers 466 can be used to receive light transmitted from the inner fiber 464.

Figure 4E:
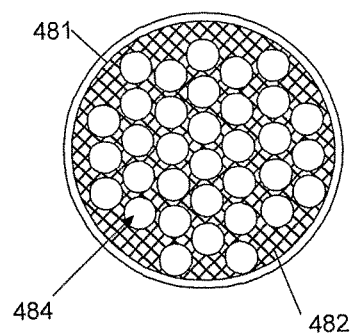

FIG. 4e shows another embodiment of the sensing element which contains a multitude of optical fibers 484 stabilized in a medium 482 enclosed in a sheath or ferrule 481. The fibers are arranged in an arbitrary or random pattern of light emitters and light receivers. Each fiber is attached to an individual light source or light sensor, and/or more than one fiber is coupled optically to share a light emitter or sensor.

Figure 5A:
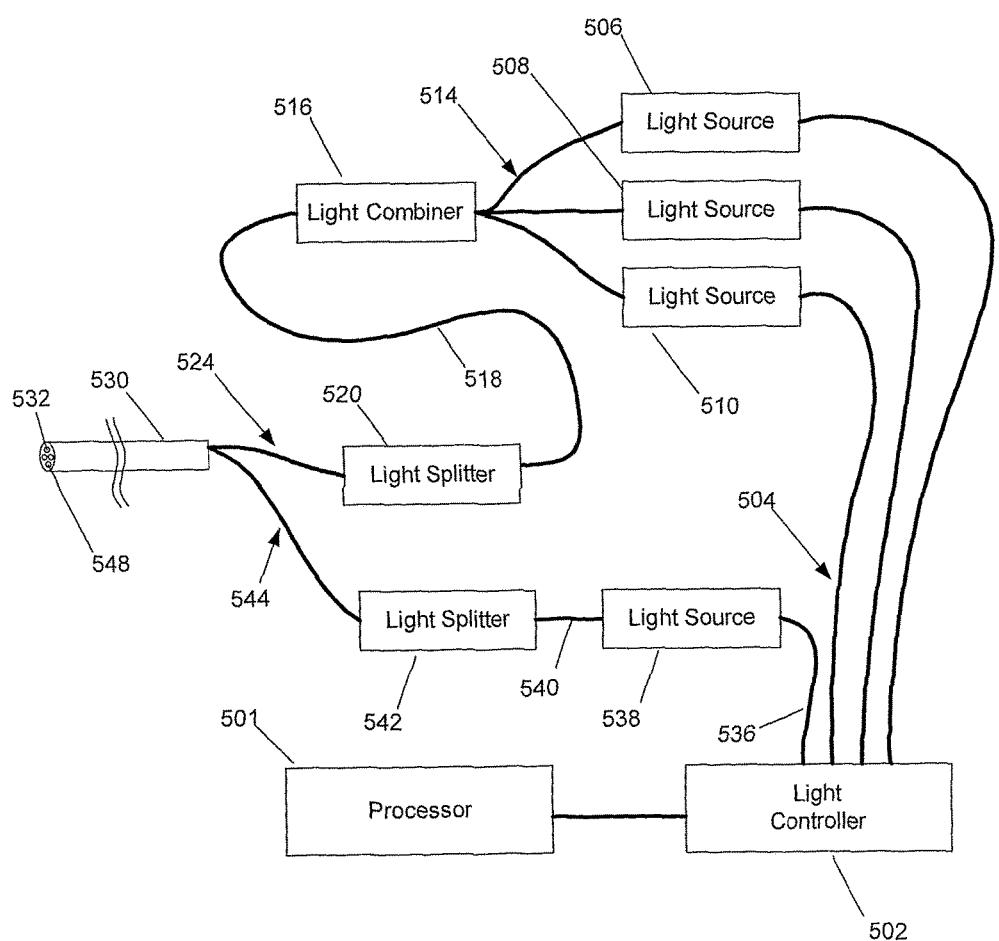
FIG. 5a is a block diagram of a configuration for transmitting light for the optical sensor of FIGS. 4a-4e.

FIG. 5a schematically displays a configuration of the light emitting components for a single measurement point in one embodiment of the sensing stapler or other sensing instrument of the invention. A processor 501, contained in the base unit 120 or onboard the instrument, commands the light controller 502, which also is located either in the base unit 120 or onboard the instrument. The light controller 502 is coupled to the light sources for one sensing modality by connections 504. The light sources 506, 508, and 510 provide the light that is incident on the tissue 102. In one embodiment, these light sources are lasers with wavelengths centered at red (near 660 nm), near-infrared (near 790 nm), and infrared (near 880 nm), respectively. This configuration is used for oximetry-type sensing where one wavelength is situated at the isobestic point for light absorption in hemoglobin, one is situated at a greater wavelength, and one is situated at a lesser wavelength. Light sources 506, 508, and 510 are one, two, three, or more distinct light emitters and are laser, light emitting diode (LED), or other sources. Alternatively, these distinct light sources are a broadband light source such as a white light. If more than one light source is used, optical couplings 514 connect the sources to a light combiner 516. If more than one output is required (i.e. more than one measurement point using the same light source), optical coupling 518 takes the light into a light splitter 520. Optical couplings 524 take the light to the appropriate fiber assembly 530. Light is transmitted out of the fiber assembly at the fiber end 532 on the tip. This tip is as depicted in FIG. 4a.

The light controller 502 controls the light emitter for one or more sensing modalities. In this embodiment, there are two optical sensing modalities: oximetry-type tissue oxygenation sensing and fluorescence sensing. Coupling 536 allows the light controller to control light source 538. Light source 538 is a high power blue LED with a center wavelength of 570 nm. This light emitter is a laser, LED, or other light source. This source is composed of one or more sources that emit light at one or more wavelengths or a broadband light source emitting at a spectrum of wavelengths. Optical filtering can also be performed on a broadband light source to produce the desired spectral output. The light from light source 538 is coupled optically 540 to a light splitter 542 if more than one measurement point uses the same source. Optical coupling 544 connects the light to the optical cable assembly 530, and light is emitted at tip 548.

In another embodiment of the invention, the light from optical fibers 524 and 544 is combined and the light is emitted from an optical fiber assembly as described in FIG. 4b, 4c, or 4d (emitter as fiber 464). In a further embodiment, the light from optical fibers 524 and 544 is split, or combined and split, into multiple fibers to be used with a cable assembly as shown in FIG. 4d (emitters as fibers 466) or FIG. 4e.

Figure 5B:
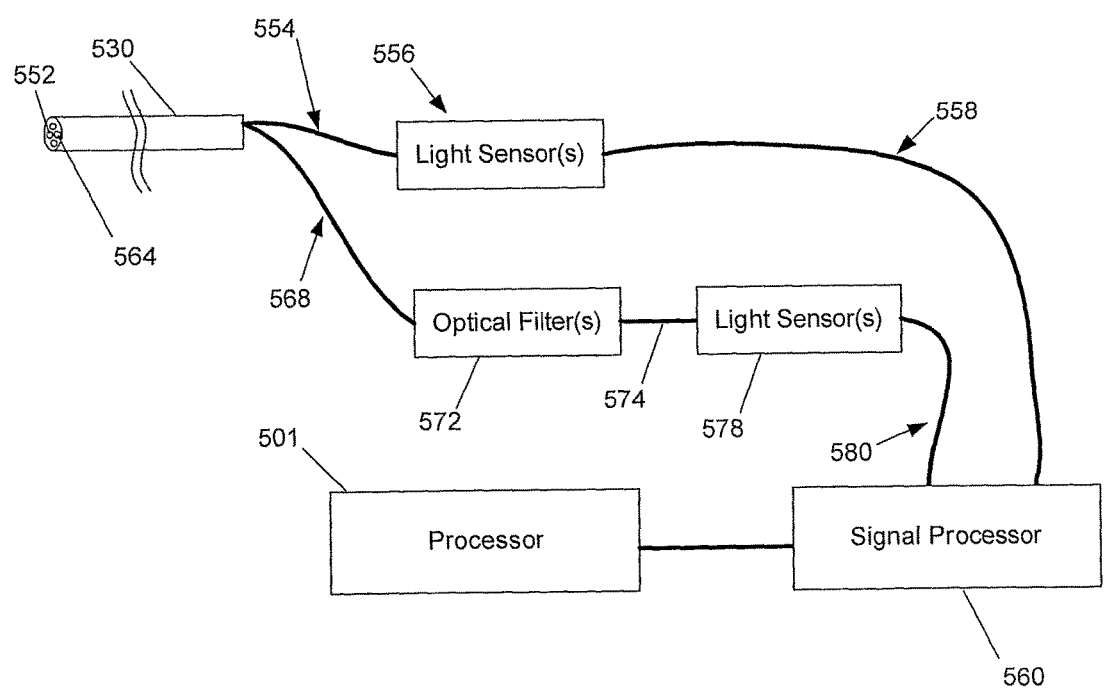
FIG. 5b is a block diagram of a configuration for receiving light for the optical sensor of FIGS. 4a-4e.

FIG. 5b schematically displays a configuration of light receiving components for a single measurement point in one embodiment of the sensing stapler or other sensing instrument 101. Light from the emitter described in FIG. 5a is incident upon the tissue being queried and the transmitted and/or reflected light passes into the tip 552 and returns through the optical cable assembly 530. Optical coupling 554 directs the light to light sensors 556. In one embodiment, light sensor 556 is an avalanche photodiode. Sensor 556 is, but is not limited to, conventional photodiodes, avalanche photodiodes, CCDs, linear CCD arrays, 2D CCD arrays, CMOS sensors, photomultipliers tubes, cameras, or other light sensing devices. In a further embodiment, light sensor 556 is a spectrometer or equivalent device that measures light intensity at one or more discrete wavelengths. In a still further embodiment, light sensor 556 is a set of selective photodiodes tuned to the wavelengths of emitted light from light sources 506, 508, and 510. Selective photodiodes are either naturally tuned to specific wavelengths or coupled with an appropriate optical filter. Light sensors 556 are coupled 558 with a signal processor 560. The signal processor 560 performs filtering, demodulating, frequency analysis, timing, and/or gain adjustment, and/or other signal processing tasks. The signal processor 560 is coupled with the processor 501 where further calculations, analysis, logging, statistical analysis, comparisons with reference, comparisons with database, visualization, notification, and/or other tasks are performed or directed.

Light from the emitter described in FIG. 5a is incident upon the tissue being queried and the transmitted and/or reflected light also passes into the tip 564 and returns through the optical cable assembly 530. Light is directed via optical coupling 568 to optical filters 572. In the fluorescence sensing modality, the optical filter 568 is a band pass or other filter that blocks the incident, excitation light while allowing the fluoresced light to pass. Filter 572 is also useful to block the emitted light from other sensing modalities and/or other light including ambient light. The filter light is coupled optically via coupling 574 to light sensors 578. In one embodiment, light sensor 578 is an avalanche photodiode. In other embodiments, light sensor 578 is the same form as light sensors 556. Light sensors 578 are coupled 580 with the signal processor 560 which is in tern coupled with the processor 501. The processor 501 and signal processor 560 perform the same functions as described previously with reference to FIG. 5a.

Figure 6A:
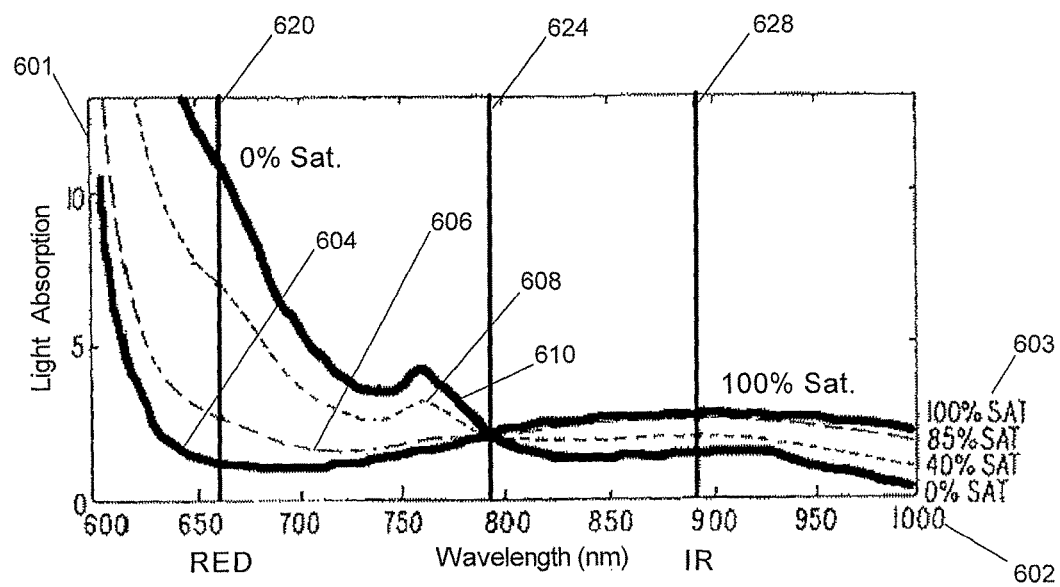
FIG. 6a is a graph showing the relationship between light absorption and incident wavelength for varying tissue oxygen saturation.
Figure 6B:
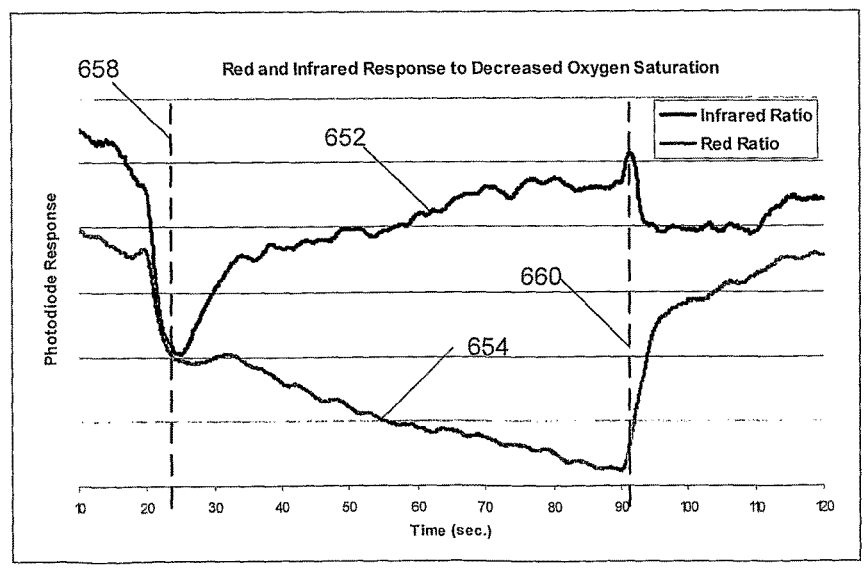
FIG. 6b is a graph showing an example of light absorption in tissue during de-oxygenation and re-oxygenation.

FIGS. 6a and 6b show plots that are used to describe oximetry sensing modality. FIG. 6a shows the relationship between light absorption 601 and light wavelength 602 for a range of tissue oxygenation levels 603. The vertical lines 620, 624 and 628 correspond to the wavelengths of 660 nm, 790 nm and 880 nm respectively. The light absorption 601 for the range of oxygen saturation levels 603 is different for each of the wavelengths. As oxygen saturation 603 decreases, the absorption increases for red light 620 and decreases for near-infrared light 628. At the isobestic wavelength near 624, light absorption is invariant to oxygen saturation. This wavelength can be used for calibration and for normalization of the signal to allow for consistent readings regardless of optical density of the tissue. One embodiment of the oxygen sensing modality emits light at the isobestic wavelength, one wavelength greater than the isobestic and one wavelength less than the isobestic, and senses the absorption responsive to the measured response.

Other embodiments emit one or more wavelengths of light and measure the transmitted, reflected, or otherwise measurable light to determine the absorption, slope of the absorption function, or other characteristics of the response that can be related to the blood oxygen saturation and tissue health.

FIG. 6b shows a plot that represents an experiment used to verify the relationship between oxygen saturation and light absorption. Red light at 660 nm represented by 652 and near infrared light at 880 nm represented by 654 are used to illuminate a section of tissue. At the time marked by 658, blood supply to the tissue is occluded. At the time marked by 660, the blood supply is restored. As blood supply is restricted and tissue oxygen saturation drops, the transmitted light intensity (inverse of absorption) increase for near infrared light 620 and decreases for red light 654.

Figure 6C:
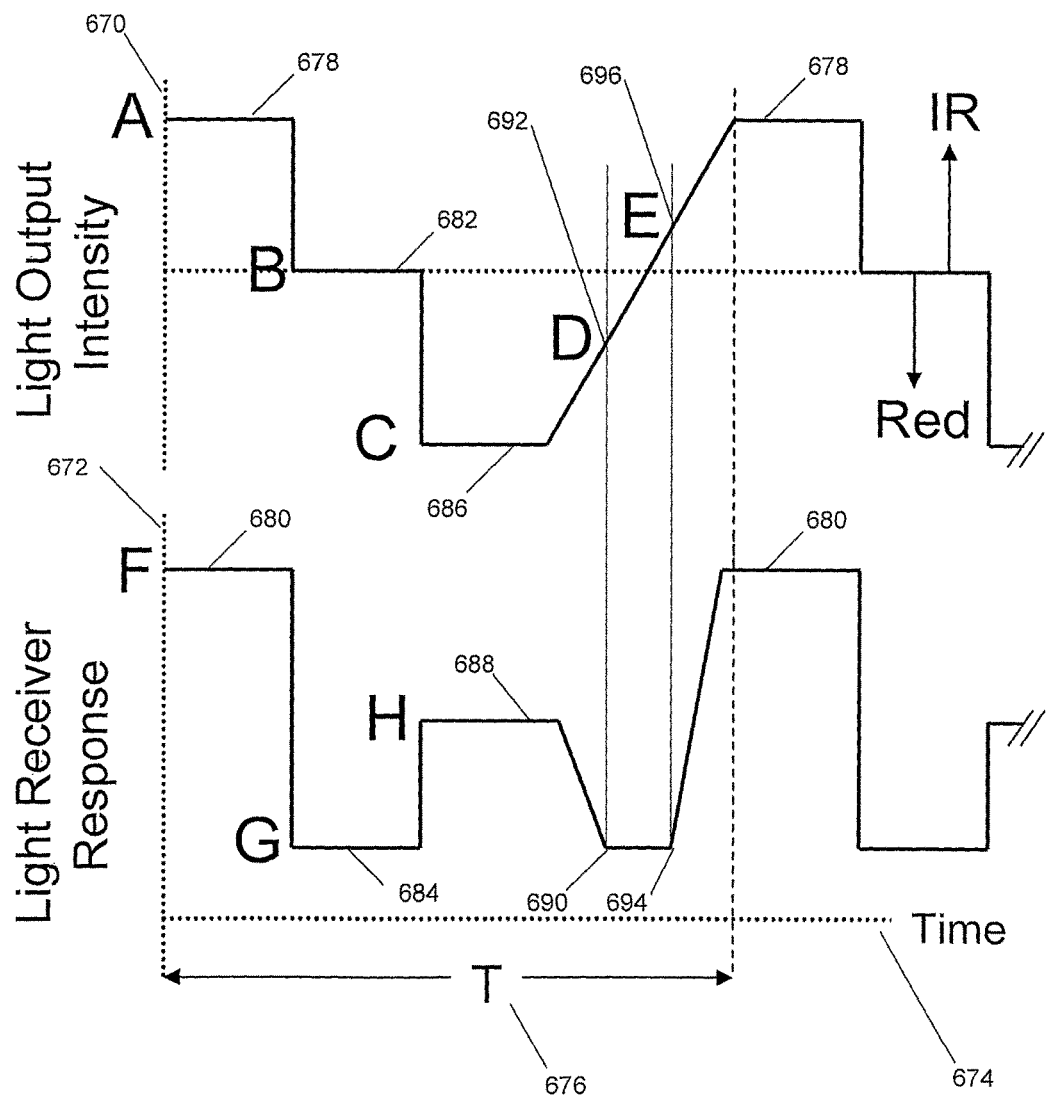
FIG. 6c is a timing diagram for an oximetry-type algorithm according to an embodiment of the present invention.

FIG. 6c shows a timing diagram and representative response for an algorithm according to the present invention used for oximetry-type oxygen saturation level sensing. The algorithm provides for a robust method of sensing oxygenation that results in a response that is minimally responsive to tissue type, color, thickness, or other properties. The timing diagram in FIG. 6c presents the method when two wavelengths of light (red and infrared) are used. It is extendable to other numbers of sources, and other types of sources and sensors.

The diagram of FIG. 6c shows the output light intensity 670 and the responsive light received 672 with respect to time 674 over a time period or cycle length 676. In one embodiment, the light emitter is a bi-color, bi-polar LED that emits red (660 nm) and infrared (880 nm) light; when a positive voltage 678 is applied, infrared light is emitted, and when a negative voltage 680 is applied, red light is emitted.

The light output intensities and corresponding response intensities are denoted with letters in the following description for use in the equations hereinbelow. In each cycle 676, red light is emitted with intensity 678 (A) and the corresponding sensed light intensity 678 (F) is recorded. Light is then shut off 682 (B) and the corresponding received light intensity 684 (G) is recorded as a baseline. Infrared light is emitted with intensity magnitude 686 (C) and the corresponding sensed light intensity 688 (H) is recorded. To make the tissue response more invariant to tissue properties other than oxygenation (i.e. tissue optical density and thickness), the maximum intensities where light can no longer sufficiently pass through (or other transmission method) the tissue and return to the sensor. Light intensity is ramped from 686 to 682. At time 690, the signal is lost and the output intensity 692 (D) is recorded. Light intensity is ramped from 682 to 678. At time 694, the signal is regained and the output intensity 696 (E) is recorded. The times 690 and 694 and corresponding intensities 692 and 696 are determined by a simple threshold on received intensity 672.

In another embodiment, these levels are determined by placing a threshold on a moving average, integration, derivatives, curve fitting, or other methods. Described is one embodiment of the timing for a robust oxygenation-type algorithm. Other functionally identical or similar embodiments exist.

A measure related to tissue oxygenation can be calculated responsive to the output and corresponding receiver light intensities. Initially, the "red ratio" is defined and is evaluated as (H-G)/(C-D), and the "infrared ratio" is defined and is evaluated as (F-G)/(A-E), where the letters correspond to the magnitudes of the light intensities as described. The numerator of the ratios determines the response after eliminating effects of ambient or other external light sources. The denominator of the ratios normalizes the response by the amount of light that was actually incident on the tissue that made it back to the sensor. The oxygenation is responsive to the two ratios. The "relative oxygen saturation" is defined as the red ratio divided by the infrared ratio and is related, not necessarily linearly, to the oxygen saturation of the tissue being measured. The relative oxygen saturation is useful for determining trends in oxygenation and also as a comparison with respect to time and/or a separate reference sensor. One important difference between the technique described and that of standard pulse oximetry is that the employed algorithms are not based on pulsatile flow in the tissue. Therefore, it is possible to acquire the tissue oxygen saturation even if blood flow is non-pulsatile, or even not flowing. Further, the algorithms incorporated improve measurement robustness and stability by compensating for tissue thickness and type (or more specifically, the optical impedance of the tissue being measured).

Figure 7:
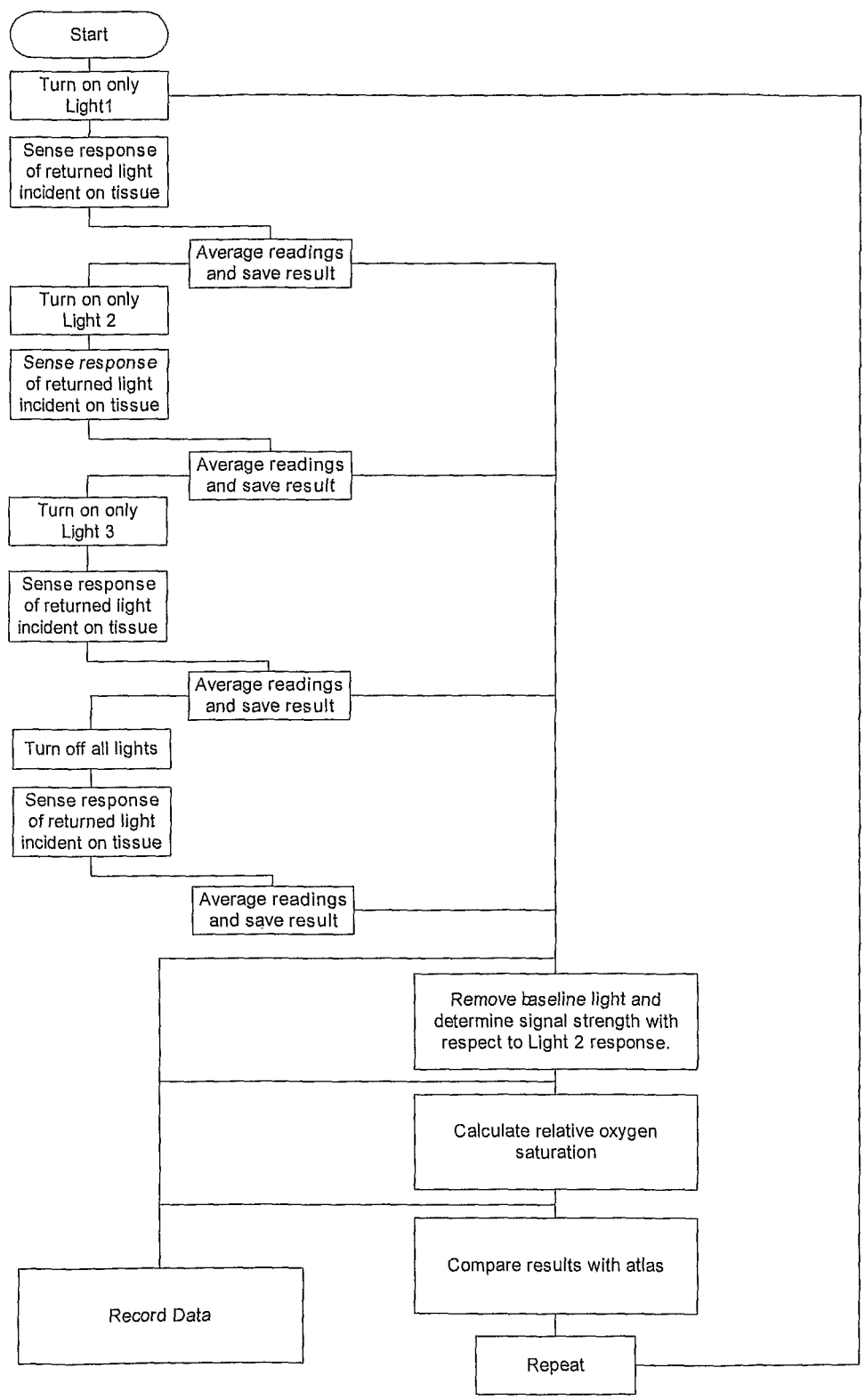
FIG. 7 is a flowchart for oximetry-type oxygenation sensing according to an embodiment of the present invention.

FIG. 7 is a flowchart for one inventive embodiment of the oxygen sensing modality based on oximetry. This embodiment uses oximetry-type techniques for determining the light response from tissue responsive to three excitation wavelengths. These three wavelengths can include those described earlier: one red light source, one infrared light source, and one light source at the isobestic wavelength. The measured response in the absence of an excitation light is used as a baseline intensity and subtracted from the three measured responses. All raw data is logged, and a calculation is performed to convert the light absorption for the three wavelengths to a value related to tissue oxygenation. The calculated values are compared to a database or other previously acquired or determined dataset. Although exactly three wavelengths are shown, other embodiments use one or more wavelengths of excitation light. In further embodiments, the intensities for each of the excitation lights may be ramped in intensity as detailed in FIG. 6c to create a more robust measurement that is invariant to tissue optical density.

Figure 8A:
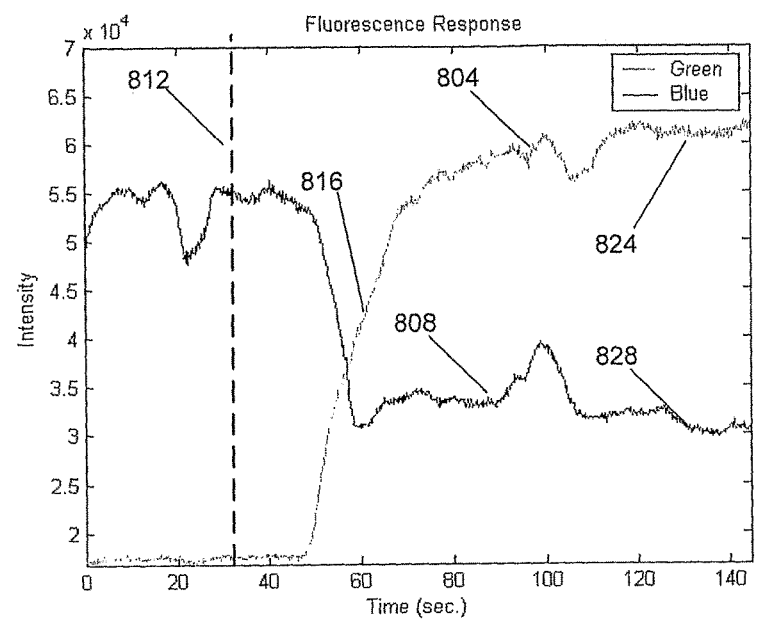
FIG. 8a is a graph showing a response to incident light and fluoresced light as fluorescent dye is introduced into a living tissue.
Figure 8B:
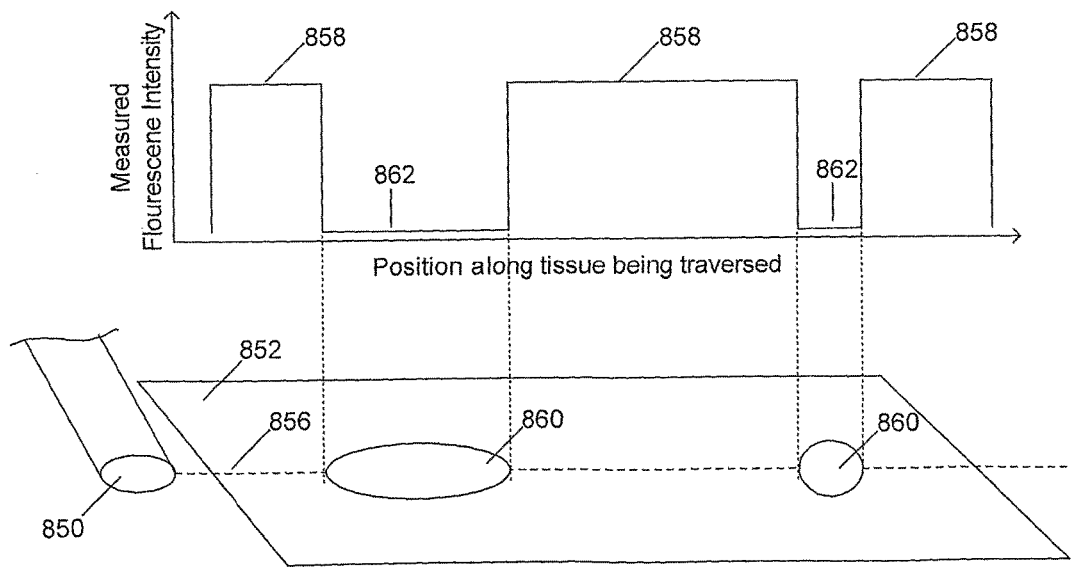
FIG. 8b shows a simulated representative fluorescent sensor response as the sensor traverses perfused and non-perfused tissue according to an embodiment of the present invention.

FIGS. 8a-8b show typical results for experiments with the fluorescent sensing modality. Tissue perfusion can be assessed using fluorescence. Biofluorescence can be achieved using a variety of commercially available products. One example is fluorescein isothiocyanate which is an intravenously injected, biocompatible dye which fluoresces yellow-green (peak near 520 nm) when illuminated with an blue/ultraviolet (peak near 488 nm) source. This sensing modality can be incorporated into the configurations shown to allow for multi-modality sensing, or included as a stand-alone sensor. A dense array of sensors enables imaging of the perfusion along a line and a determination if there are patches of poorly perfused tissue in an otherwise healthy region. Stapler fluorography can also utilize fluorescent microspheres and quantum dots. These entities can be used as molecular tracers to characterize tissue substructure such as vessels, or bile ducts. In addition, inflammatory mediators and other biomolecules germane to anastomosis viability can be detected though fluorography at a staple line.

FIG. 8a represents the measured intensity of the transmitted and/or reflected incident light 808 and the measured intensity of the fluoresced response 804 to the incident light source. The plot shows the light intensity centered at the incident and fluoresced wavelengths as fluorescent dye is instilled into or perfused though the bloodstream at time 812. As the dye perfuses into the tissue being measured, the fluorescent response becomes more evident and the sensed incident light decreases. The slope, rise time, magnitude, steady state value, shape, integral, or other characteristics and curve properties of the onset of fluorescence 816 can be used to determine characteristics of the tissue perfusion and health. The steady state values of the fluoresced light 824 and incident light 828 can be used to determine tissue perfusion and overall health and/or the type of tissue. The measured response can be used alone, with a previously collected dataset from the same or other patients, or in conjunction with a reference signal. Infusion of the fluorescent medium can be introduced either in a single injection, or it can be ramped up in either continuously or in discrete increments. By varying the amount of fluorescent medium introduced into the patient, continuous or multiple measurements can be performed of the characteristics of the onset of fluorescent response.

FIG. 8*b* shows typical results for passing a fluorescence sensing probe 850 across a tissue sample 852. In one case, the fluoresced response 858 serves as a baseline for healthy tissue 856 and the decreased intensity 862 corresponds to a region of tissue that is depleted of blood supply 860. Alternately, the baseline intensity can be the lower level 862 and the fluorescence peaks to 858 as the probe passes over a blood vessel 860. This scanning technique can be used to determine sections of tissue with proper perfusion. In one embodiment, multiple sensor probes 850 are integrated in a linear, grid like, or other arrangement on the surface of a surgical instrument such as a stapler, a retractor, a grasper, a clip applier, a probe, a scope, a needle, a catheter, a mesh substrate, or other device.

Figure 9:
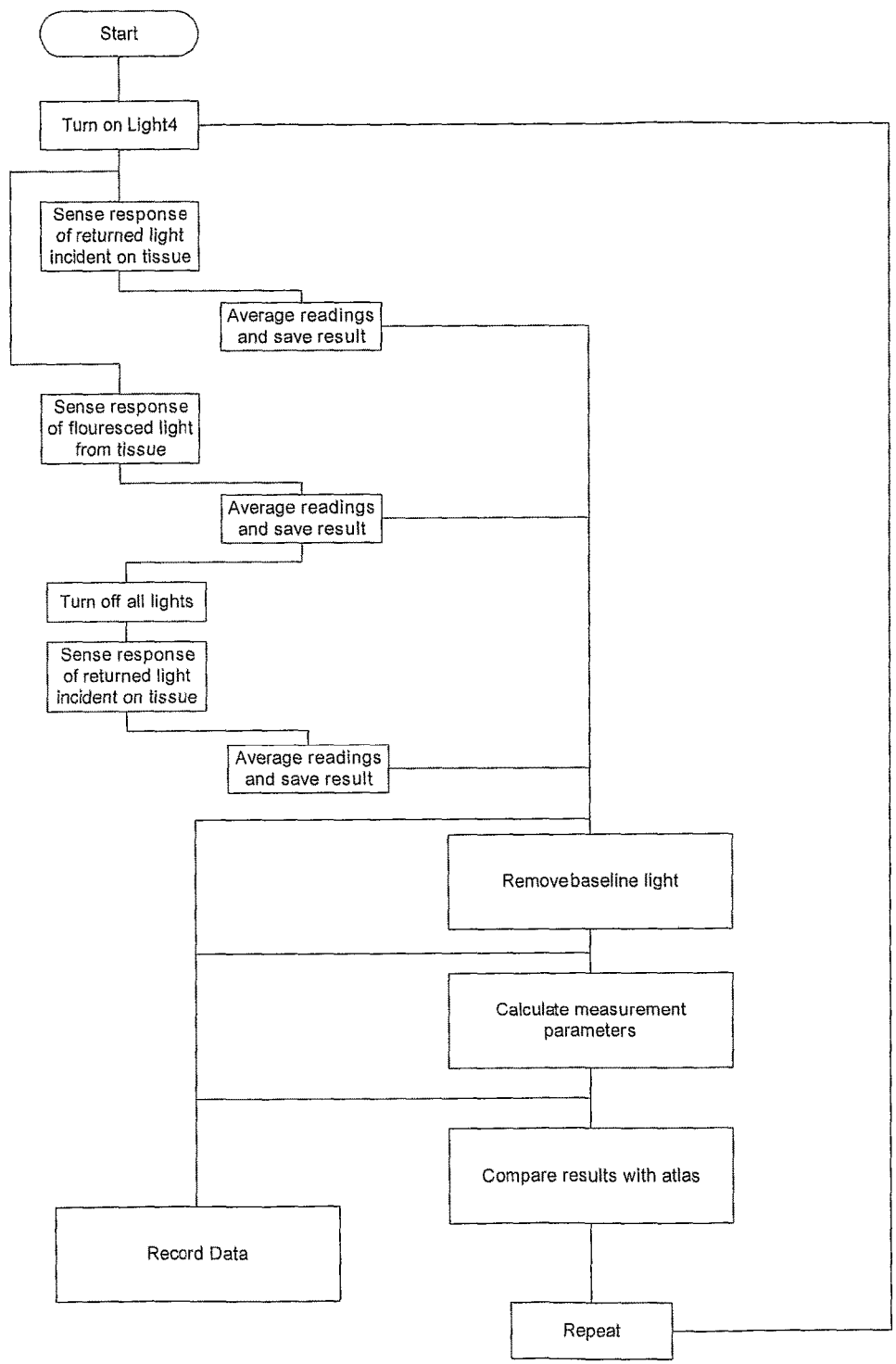
FIG. 9 is a flowchart for fluorescence sensing according to an embodiment of the present invention.

FIG. 9 is a flowchart for one embodiment of the inventive fluorescence sensing modality. Light containing or centered at a wavelength that excites the fluorescent medium is transmitted into the tissue. The light intensity of the fluorescent response is then measured; optical filters, wavelength selective light receivers, or a spectrometer are used to differentiate excitation light and fluorescent response. The measured response in the absence of an excitation light is used as a baseline intensity and subtracted from the fluorescent response. All raw data is logged, and a calculation is performed to determine one or more properties of the onset of the fluorescent response and the steady state value as described earlier. The calculated values are compared to a database or other previously acquired or determined dataset. This sensing modality can be combined with that described by the flowchart of FIG. 7. In one embodiment, both oximetry-type sensing as represented in FIG. 6 and FIG. 7 and fluorescence-type sensing as represented in FIG. 8 and FIG. 9 are combined into a single integrated device. The schematic diagram shown in FIG. 5 shows how light sources and detectors for both sensing modalities can be integrated into a single system. Other sensing modalities, optical or other types, can be combined to perform multi-modality sensing on the working surface of surgical instruments.

Figure 10A:
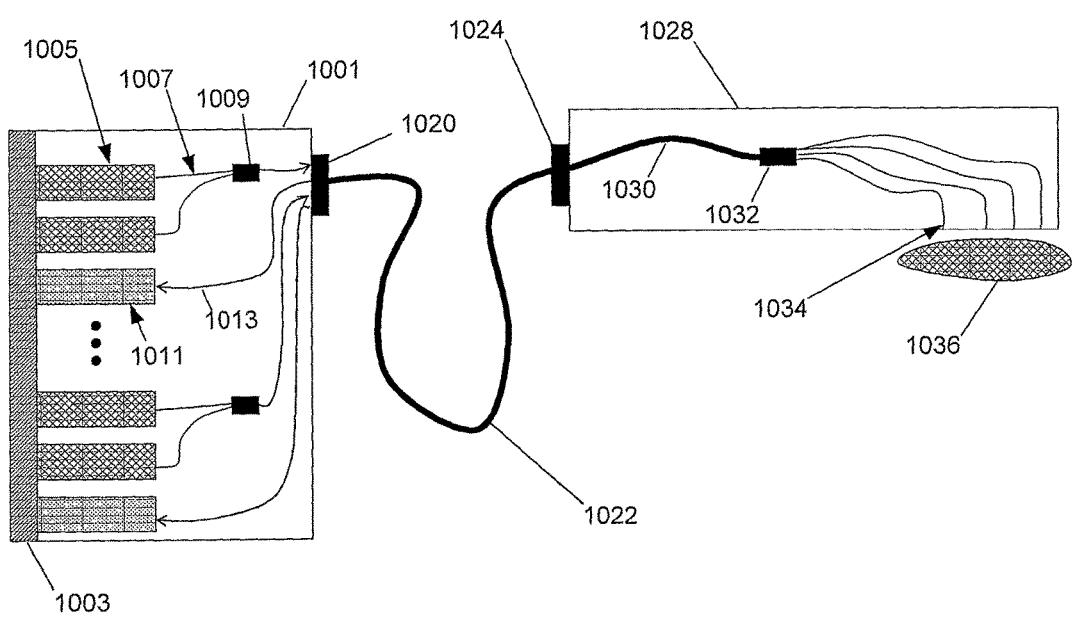
FIG. 10a illustrates a system according to an embodiment of the present invention with light sources and receivers external to an instrument.
Figure 10B:
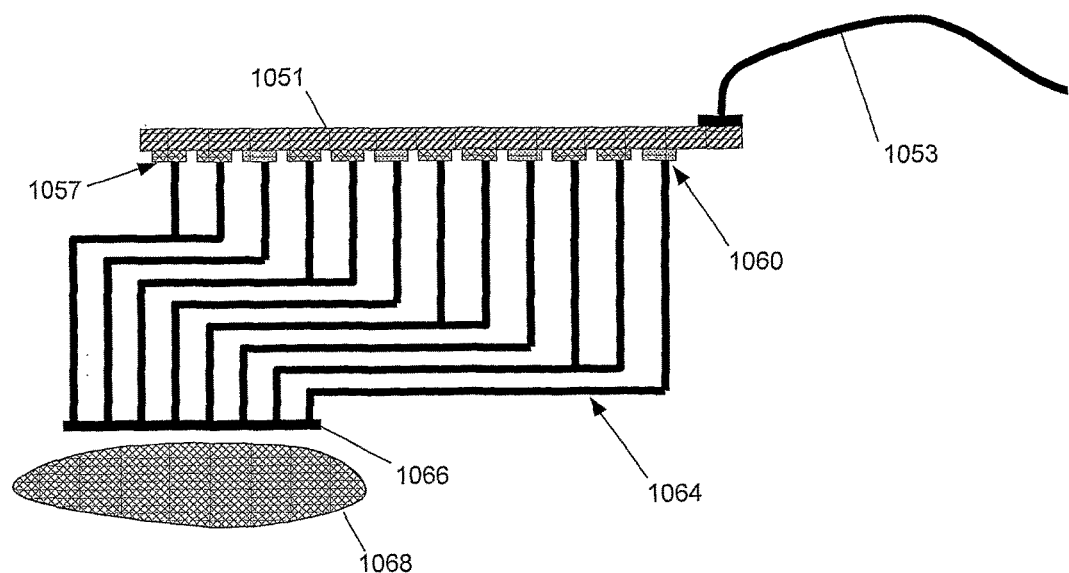
FIG. 10b illustrates a system according to an embodiment of the present invention with light sources, light receivers, and light guides internal to an instrument.
Figure 10C:
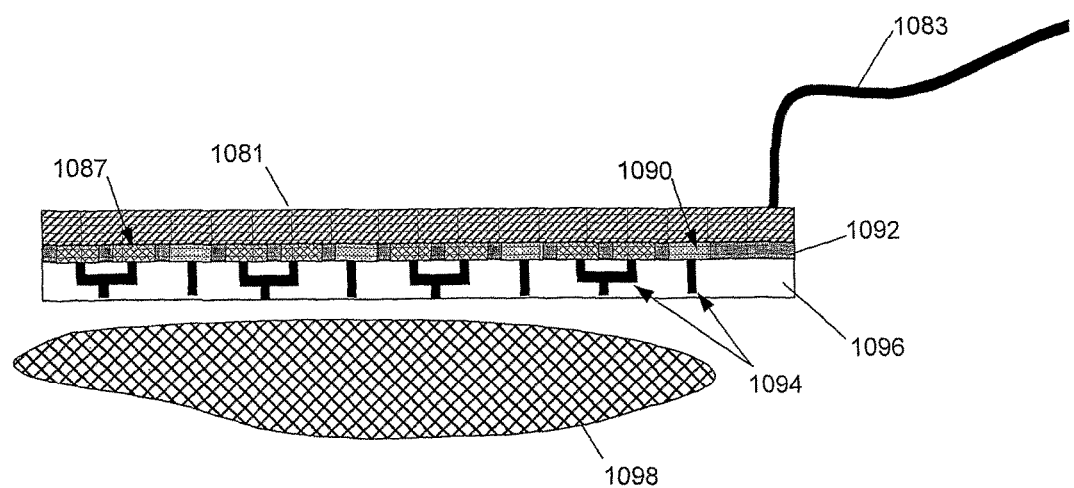
FIG. 10c illustrates a system according to an embodiment of the present invention with micro fabricated internal light sources, light receivers, and light guides.

FIGS. 10*a*-10*c* present techniques that can be used to perform said oximetry-type and/or fluorescence-type sensing. These techniques can be combined with other sensing modalities including optical sensors, electrical sensors, chemical sensors, mechanical sensors, MEMS sensors, nano sensors, biochemical sensors, acoustic sensors, immunologic sensors, fluidic sensors, or other types of sensors.

FIG. 10*a* shows a surgical stapler embodiment of the system configuration where all light sources and detectors are located external of the surgical instrument's body. In this embodiment, the light sources and detectors are located in control unit 1001 and sensing, control, calculations, and communications are performed in control electronics 1003. In one embodiment, control unit 1001 constitutes durable equipment and instrument 1028 is a potentially disposable device. For each measurement point, one or more light sources 1005 are coupled optically via 1007 to a light combiner 1009. The light sources can be narrowband emitters such as LEDs and lasers and/or broadband light sources such as white lights and can be use with or without additional optical filtering. For the same measurement point, one or more light receivers 1001 are coupled optically via 1013. The light receivers can be photodiodes, photodiode arrays, avalanche photodiodes, photomultiplier tubes, linear and two dimensional CCDs, CMOS sensors, spectrometers, or other sensor types. The light traveling through couplers 1009 and receiver couplings 1013 are coupled to an optical connector 1020. In one embodiment, this connector is a standard high density fiber optic connection and coupling 1022 is a standard high density fiber optic cable. Coupling 1022 connects to the sensing instrument 1028 at connector 1024 and passes through fiber 1030 to a breakout 1032. Sensor points 1034 can be either single fibers or multi-fiber sensor tips as represented in FIGS. 4*a-e*. The sensor tips transmit the incident light onto tissue 1036 and/or receive the reflected, transmitted, and/or fluoresced light from said tissue.

FIG. 10*b* depicts an embodiment where the light emitting and receiving components are located onboard a surgical instrument. In this embodiment, circuit board 1051 is mounted in or on the instrument and coupled via 1053 to a control unit. Coupling 1053 is electrical, optical or wireless. Attached to circuit board 1051 are light sources 1057 and light receivers 1060. In one embodiment, they are standard surface mount LEDs and photodiodes. Light guides, light combiners, and/or light splitters 1064 direct light to and from the sensing working surface 1066 of the instrument to and from the tissue being monitored 1068. In one embodiment, 1051 represents a flexible medium and light sources and receivers 1057 and 1060 represent alternative light sources and emitters such as organic LEDs and organic photo detectors.

FIG. 10*c* shows a further embodiment where the light emitting and receiving components are located onboard a surgical instrument. In this embodiment, the electronics are microfabricated into a compact sensing element that can fit onto the working surface of the instrument. As described hereinabove, coupling 1083 connects the circuit to an external controller. The circuit is built on base 1081. Light emitters 1087 and detectors 1090 are embedded in layer 1092. Coupled to the light sources and detectors are micro fabricated light guides, light combiners, and/or light splitters 1094 in layer 1096. The light guides direct light to and from the tissue being monitored 1098.

Figure 11A:
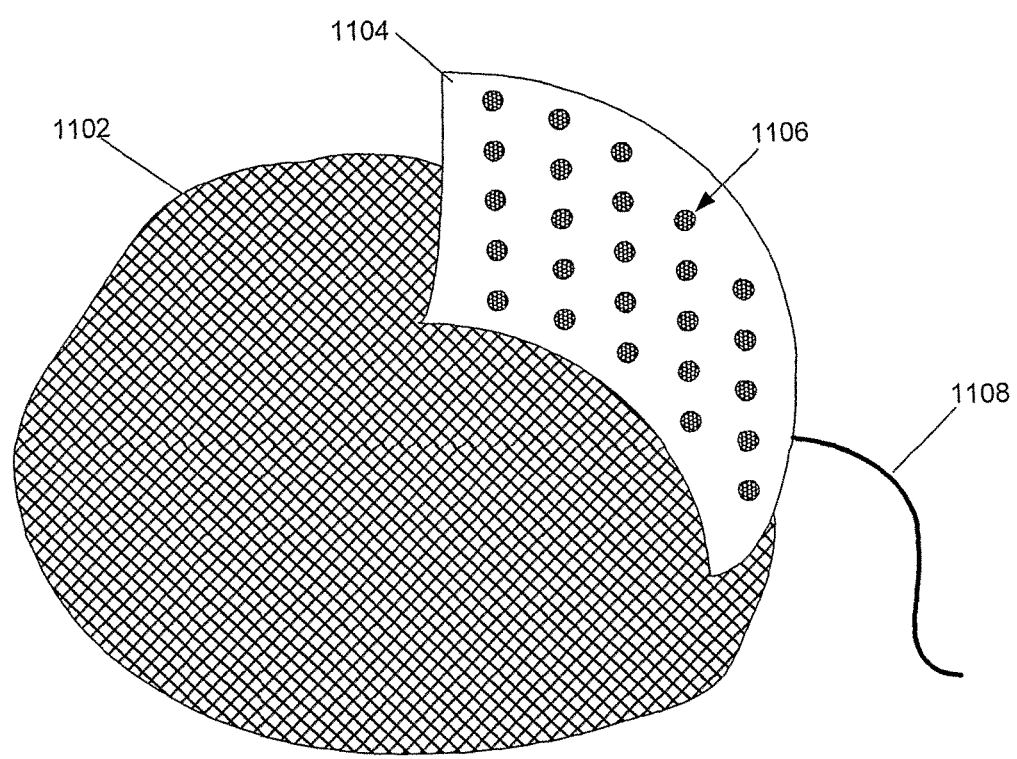
FIG. 11a illustrates a sensor configuration according to an embodiment of the present invention where sensing elements are situated on a flexible substrate.
Figure 11B:
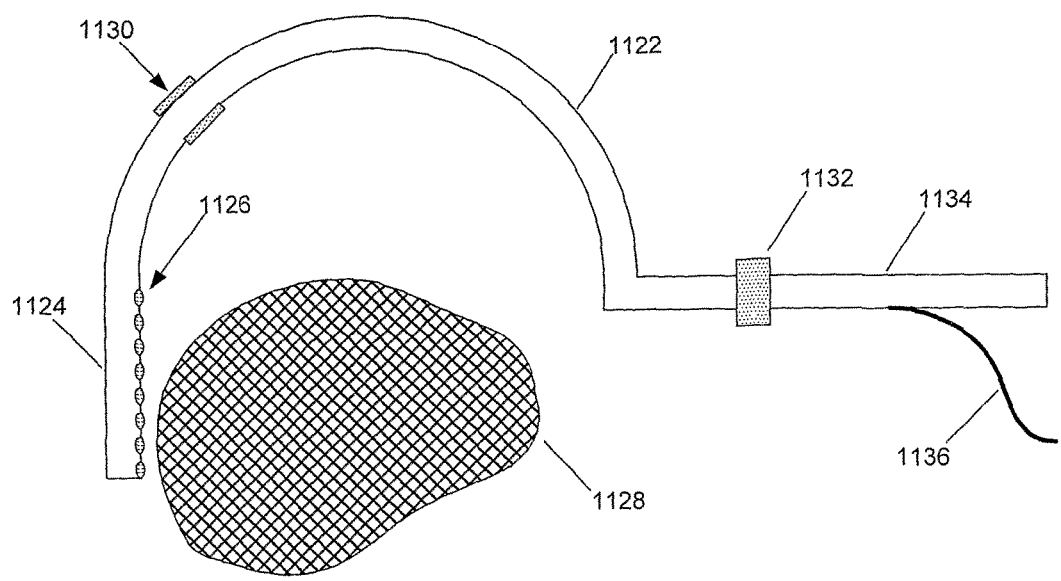
FIG. 11b illustrates a sensor configuration on a surgical retractor for open surgery according to an embodiment of the present invention.
Figure 11C:
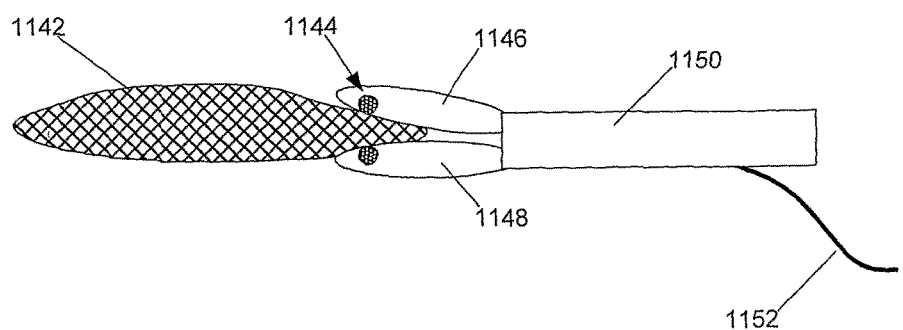
FIG. 11c illustrates a sensor configuration on a grasper for minimally invasive, laparoscopic surgery according to an embodiment of the present invention.

FIGS. 11*a*-11*c* depict further embodiments of sensing surgical instruments and devices according to the present invention. FIG. 11*a* shows a sensing flexible mesh 1104 that contains sensing elements 1106. Sensing elements 1106 can be electrical, optical, chemical, or other sensor types used to monitor the tissue 1102 or other operational parameters. The mesh 1104 can mold to the surface of tissue 1102. In one embodiment, sensors 1106 are oxygenation sensors as described previously and are used to monitor the tissue health and other tissue properties. In addition, when there is a plethora of sensors, mapping of the oxygenation levels of the surface of the tissue 1102 can be performed. If the location of the sensors is known with respect to the tissue or imaging device, then this mapping can be overlaid on medical imaging information including x-ray, computed tomography, magnetic resonance imaging or ultrasound images and volumes, or it can be overlaid on a video signal from an endoscope or other camera. In another embodiment, sensors 1104 are electrical sensors that are used for EMG or other electrical activity or impedance mapping. The mesh is coupled via 1108. Coupling 1108 is electrical, optical, or wireless. Sensors 1104, in optical sensing modalities, are either onboard electronics or the distal tips of optically coupled emitters and detectors.

The sensing surgical mesh can be generally described as a rigid or flexible surface that contains sensing elements. The sensing elements detect information about the tissue upon which they are placed. The mesh is flexible, or preshaped to conform to the tissue being monitored. In one embodiment wherein the mesh is bioabsorbable, the mesh is made of bioabsorbable polymers similar to those used in conventional absorbable sutures. In another embodiment wherein the mesh is durable, the mesh is made of polymers similar to those used in conventional non-absorbable sutures. In a further embodiment, the substrate is an adhesion barrier material, such as Seprafilm®, available from Genzyme Corp. of Cambridge, Mass. The tissue being monitored is either internal tissue, such as an organ being monitored after transplant or a bowel segment whose perfusion is to be verified, or is external tissue, such as a skin flap being monitored for reconstructive surgery, or skin being monitored for the prevention of bed sores. The mesh sensor array is either a temporary device used during a procedure (either single use or reusable), permanently implantable, or of a bio degradable, bio absorbable nature as is known in the art.

FIG. 11b shows a surgical retractor 1122. The working surface of the retractor 1124 is instrumented with sensors as previously described (i.e., with sensing elements 1106) for measuring properties of a tissue 1128. In addition to monitoring tissue properties, interactions with tissue 1128 are measured using strain gages, piezoelectric sensors, load cells, multi-axis force/torque sensors, and/or other sensors 1130 and 1132. The retractor handle 1134 is held manually by a member of the operating room staff, mounted to a frame or passive arm, or held by a robotic retraction system. Coupling 1136 couples sensors 1126, 1120, and/or 1132 to an onboard or external control interface (not shown) as described hereinabove. In one embodiment, sensors 1126 are oximetry-type sensors comprising of a plethora of multi-color LEDs and photodiodes and sensors 1130 and 1132 are either strain gages or multi-axis force/torque sensors respectively for measuring the forces incident upon the tissue during retraction while simultaneously monitoring oxygenation levels. In the case of a robotic retraction system or other robotic-assisted surgery scenario, the sensed information including interaction forces and tissue status is used to close the control loop for the robot and/or provide warnings or augment the motions of the robot manipulator.

FIG. 11c displays a surgical grasper that is instrumented with sensors 1144 mounted on grasper jaws 1146 and 1148. The grasper clamps or otherwise contacts tissue 1142 and senses oxygenation, tissue perfusion, electrical properties, chemical properties, temperature, interaction forces, grasping forces, and/or other parameters. Coupling 1152 couples sensors 1144 to an onboard or external control interface (not shown) as described hereinabove. Sensors 1144 can be placed on one or both sides of the jaw and/or on the shaft 1150 of the instrument. In one embodiment, the grasper measures the oxygenation level of the tissue being grasped while simultaneously monitoring grasping force and other tissue interaction forces.

Figure 11D:
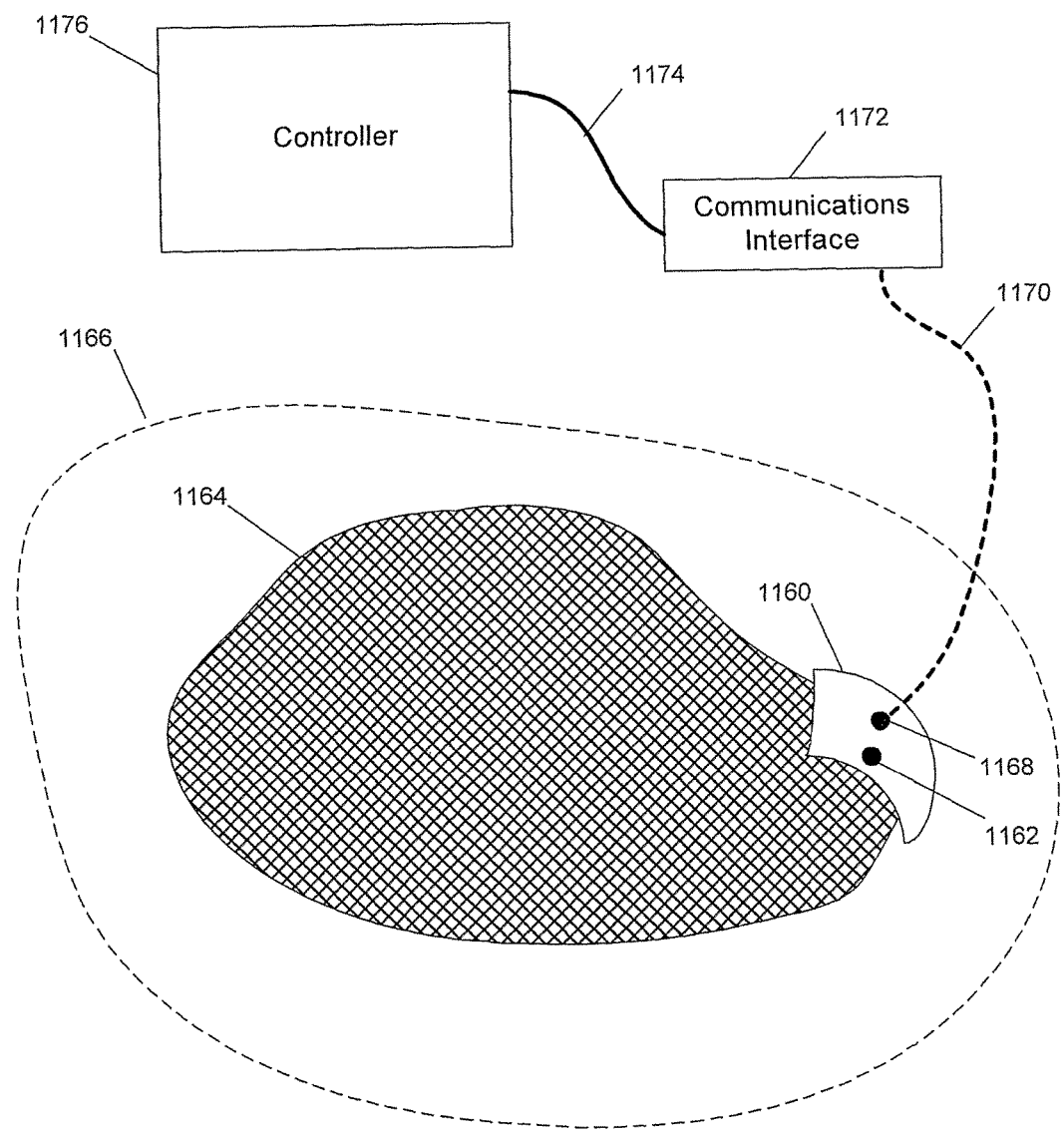
FIG. 11d illustrates a sensor configuration where sensors are implanted into the body and transmit data wirelessly according to an embodiment of the present invention.

FIG. 11d shows a configuration for a sensor implanted in the body that relays information back to a controller. Sensor device 1160 contains one or more sensing elements 1162. The sensing elements can be any of the type described earlier including oxygenation, fluorescence, tissue perfusion, general health, tissue electrical impedance, tissue electrical activity, interaction forces, pH, electromyography, temperature, spectroscopy, fluid flow rate, fluid flow volume, pressure, biomarkers, radiotracers, immunologic, chemical, nerve activity, and evoked potential, and other sensor types capable of determining characteristics of tissue. The sensor device 1160 is placed inside of, on the surface of, embedded into, or wrapped around tissue 1164. The tissue being monitored is, for example, an organ, a bowel segment, a blood vessel, a chest wall, or other biological tissue. The sensor can be temporary, permanently implantable, or bioabsorbable/biodegradable inside of body 1166. In one embodiment, the sensor device is implanted onto the bowel and used for monitoring the tissue after a procedure and for obtaining data related to short and long term outcomes. In another embodiment, the sensor is a ring that is placed around a blood vessel and is used to monitor blood flow in said vessel.

In some embodiments, one or more sensor devices on one or more tissues 1164 are communicatively coupled via 1170 to a communications interface 1172. In one embodiment, the coupling 1170 is a wireless link where the power from a radio frequency signal generated by 1172 powers the sensor device 1160 which then takes a measurement and return data via wireless coupling 1170. The communication interface is coupled via 1174 to a main control unit 1176. In another embodiment, the communications interface 1172 is a portable battery powered device that can be carried by the patient, or a fixed device placed inside or outside of a hospital or a medical professional's office for powering and monitoring the internal sensors 1160. The communication interface 1172 can conveniently obtain acute, short, and long term follow-up data about a procedure after the surgery is complete. The communications interface 1172 and controller 1176 may be one in the same. In one embodiment, the controller 1176 is the main system's base control unit 120. In another embodiment, the communication interface 1172 is directly in communication with the main system's base unit 120 or the central database 131 directly.

In a further embodiment of the system shown in FIG. 11d, the sensor device contains a MEMS sensing element and communications electronics, is placed in or on internal tissue, and communicates wirelessly with and receives power from an external radio frequency source for the purpose of post procedure patent monitoring. In another embodiment, the sensing element is made of biocompatible materials known in the art, and an attached antenna is bioabsorbable in the patient's body. The associated electronics and/or antenna can be made either bioabsorbable or biodegradable, or such that their presence does not have any significant effect on the patient, or any combination thereof.

Figure 11E:
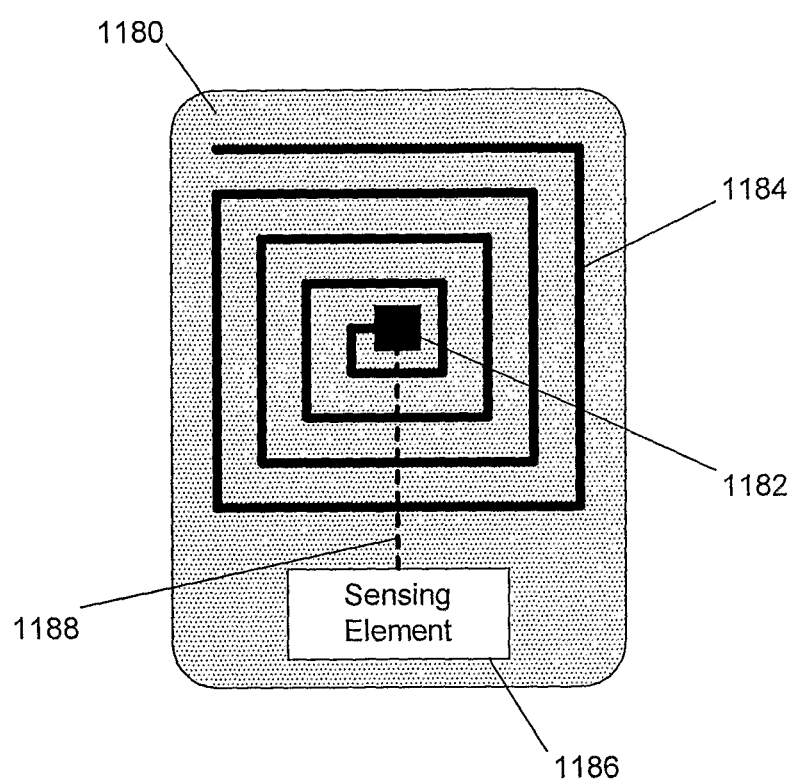
FIG. 11e illustrates a remotely powered integrated sensor and wireless transmitter according to an embodiment of the present invention.

FIG. 11e shows a detailed view of an embodiment of sensor unit 1160. The sensor unit is built into substrate 1180 which, in one embodiment, is composed of a bioabsorbable polymer as is known in the art. The sensor unit contains a communications device 1182 which is coupled to an antenna 1184. In certain embodiments, the antenna body is made of a fully or partially bioabsorbable/biodegradable polymer, and contains connected tubes that are filled with conductive and biocompatible gel or liquid. The communications device is biocompatible, and can be bioabsorbable. Coupled via 1188 to the communications device 1182 are one or more sensing elements 1186. The sensing elements can be of any of the type described earlier. In one embodiment, the sensing elements are fully or partially bioabsorbable/biodegradable.

In certain embodiments, the sensing elements and communications device obtain electrical power remotely from a radio frequency source, such as in RFID technology as known in the art, and use this power to perform sensing operations and to transmit data to communications interface 1172. The embodiment shown in FIG. 11*e* is a representative configuration of the sensor unit; other types, shapes, and configurations are understood to be included as well.

In further embodiments of the present invention, an absorbable optical fiber (such as shown in FIGS. 4*a-e*) comprises at least a core and an outer cladding made out of bioabsorbable materials. Its layers can be made out of bioabsorbable materials with different time constants for degradation. For example, the cladding is thin but of a material composition that degrades very slowly, and the core is of a composition that degrades very fast since once the cladding is degraded, the fiber is useless. This bioabsorbable optical fiber is used for the light guides for optical sensors and/or for a communicative coupling between the sensors and a controller.

Figure 12A:
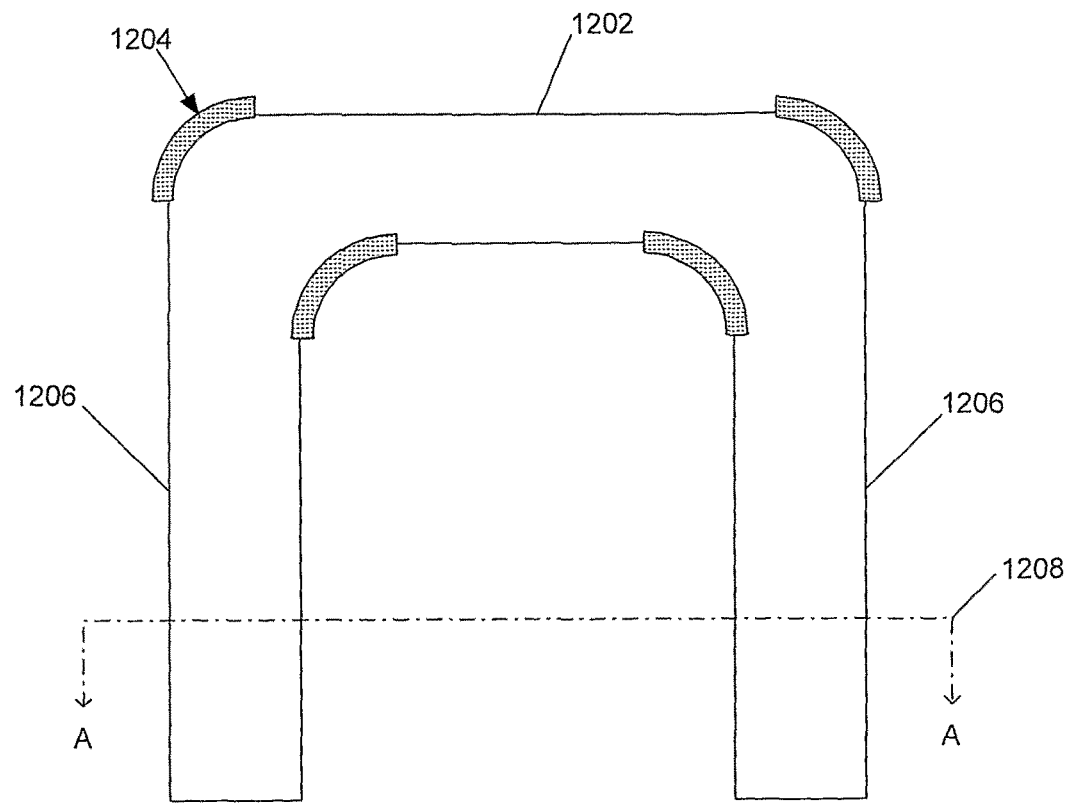
FIG. 12a shows a surgical staple or clip with sensing capabilities according to an embodiment of the present invention.
Figure 12B:
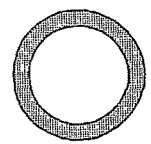
Figure 12B:
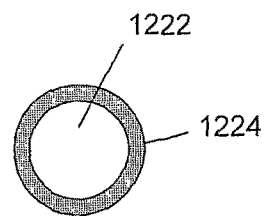

FIGS. 12*a-c* shows a surgical staple or clip with integrated sensing capabilities. The staple, clip, suture, or other fastener itself can be used as an electrode, as a strain or force sensor, or as an optical pathway. Forces pulling on an anastomosis or other tissue joining can cause failure. By placing force measuring instrumentation on either a stapler or other instrument's working surface, or on staples, clips, sutures, or other fasteners themselves, it is possible to measure the strain induced on the tissue being joined.

FIG. 12*a* shows a staple with embedded sensors. The staple can include any of the sensing modalities discussed earlier. In one embodiment, strain sensing for measuring the pulling or pushing forces exerted by tissue on the staple legs 1206 may be incorporated into the fastener. In another embodiment, strain gages 1204 are fabricated on the surface of the staple as 1204. In yet another embodiment, a coating or partial layer of a piezoelectric or resistive coating 1224 is fabricated around staple core 1222 as shown in cross-section A-A in FIG. 12*b*. In other embodiments, the staple is a hollow tube 1224 whose inner core 1222 is made of a piezoelectric, resistive, or other material or component that permits measurement or bending load on the staple legs 1206. This design is extendable to incorporating sensing capabilities into any surgical fastener including staples, clips, and sutures. The staple, clip, or other fastener is made of in whole or in part of bioabsorbable/biodegradable, biocompatible materials as known in the art.

Figure 13A:
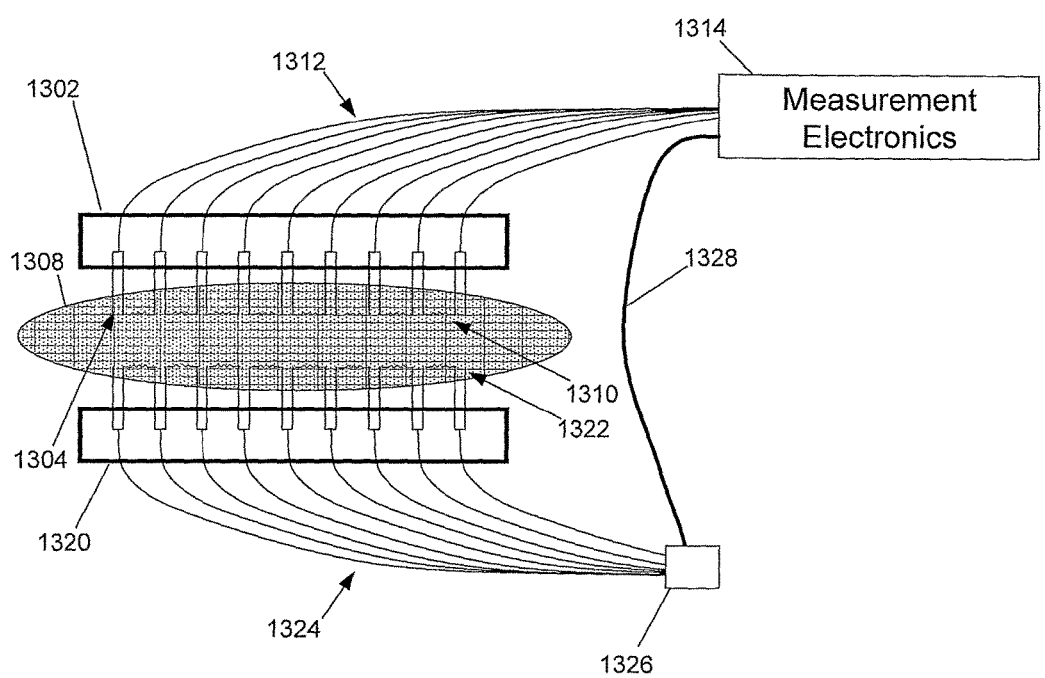
FIG. 13a illustrates a system according to an embodiment of the present invention where the staples or clips measure electrical impedance.
Figure 13B:
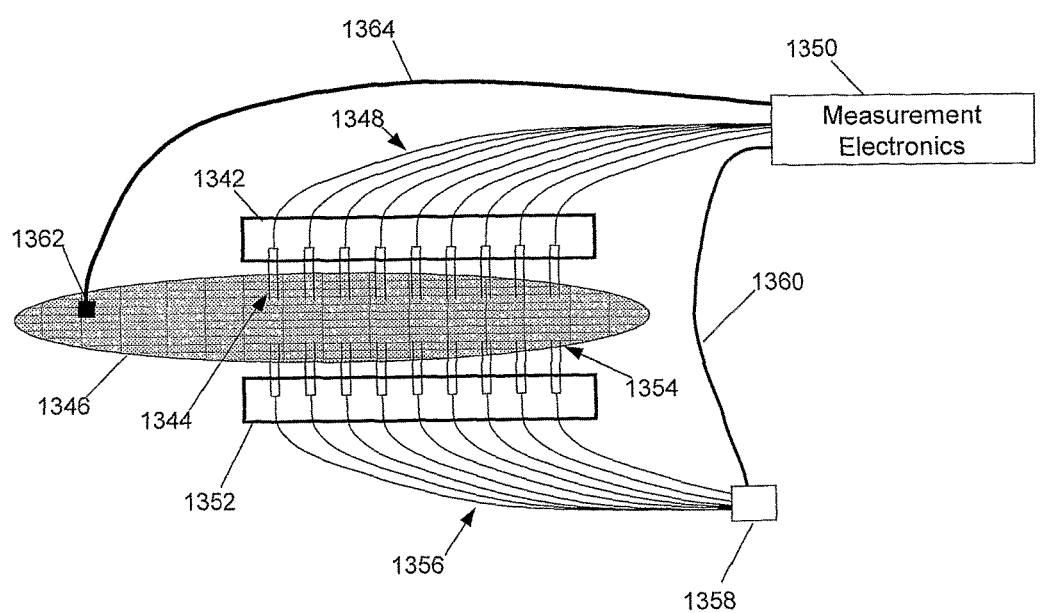
FIG. 13b illustrates a system according to an embodiment of the present invention where staples or clips and a reference sensor perform electric electrical stimulation and electrical activity sensing.

FIGS. 13*a-b* depict embodiments where a staple, clip, or other electrode is used for electrical sensing on the surface of a surgical instrument. FIG. 13*a* shows an embodiment where the instrument is used for tissue electrical impedance sensing. The electrical resistance/impedance of the tissue can be used to indicate tissue properties. By measuring electrical impedance of internal tissue at the surface of a surgical instrument, it is possible to determine the tissue's status including indications of hypoxia and ischemia. Electrodes or electrical contacts placed into the tissue are used as measurement points, the impedance measured between adjacent points and across any combination thereof. These electrodes are placed as small tips (invasive or surface contact only) on the working surface of a surgical instrument.

The instrument surface 1302 contains one or more staples, clips, or other electrodes 1304 that act as electrical contacts. The electrical contacts 1304 come in contact with tissue 1308 either on the surface or by penetrating into the tissue. The electrical impedance or resistance between the electrical contacts (either on the same staple or clip, or between adjacent or other pairs) is represented by 1310. Contacts are connected via coupling 1312 to a controller 1314 where the measurement electronics are housed. Coupling 1312 is either electrical, optical, or wireless. Additional surfaces, instruments, or opposing stapler or grasper jaws 1320 contain additional electrodes 1322. They are coupled via 1324 to an interface 1326 and further coupled via 1328 to the same or a different controller 1314, or coupled directly to the controller 1314.

FIG. 13*b* shows an embodiment where the instrument is used for tissue electrical activity sensing, including nerve and muscle stimulation and sensing. Electrical activity in tissue can be used to assess the tissue's viability. The muscular and neuronal activity that occurs in the tissue of interest is measured using techniques similar to those in electromyography: either the naturally occurring activity, or the response to an excitation due to an electrical or other impulse. Implanting electrodes into the working surface of a surgical instrument enables the viability of the local tissue to be quantified.

The instrument surface 1342 contains one or more staples, clips, or other electrodes 1344 that act as electrical contacts. The electrical contacts 1344 come in contact with tissue 1346 either on its surface or by penetrating into the tissue. The contacts are coupled via 1348 to a controller 1350 where the measurement electronics are housed. Coupling 1350 is either electrical, optical, or wireless. Additional surfaces, instruments, or opposing stapler or grasper jaws 1352 contain additional electrodes 1354. They are coupled via coupler 1356 to an interface 1358 and further coupled by coupler 1360 to the same or a different controller 1350, or coupled directly to the controller 1314. The electrical contacts can be used for both sensing and/or stimulation of the tissue or components thereof. A separate electrical contact 1362 is placed in tissue 1346. The separate contact can serve as a reference or as a source of nerve, muscle, or other stimulation that is sensed by the other electrical contacts 1344 and 1354. Reference contact 1362 is coupled via coupler 1364 to the controller 1350.

Figure 14:
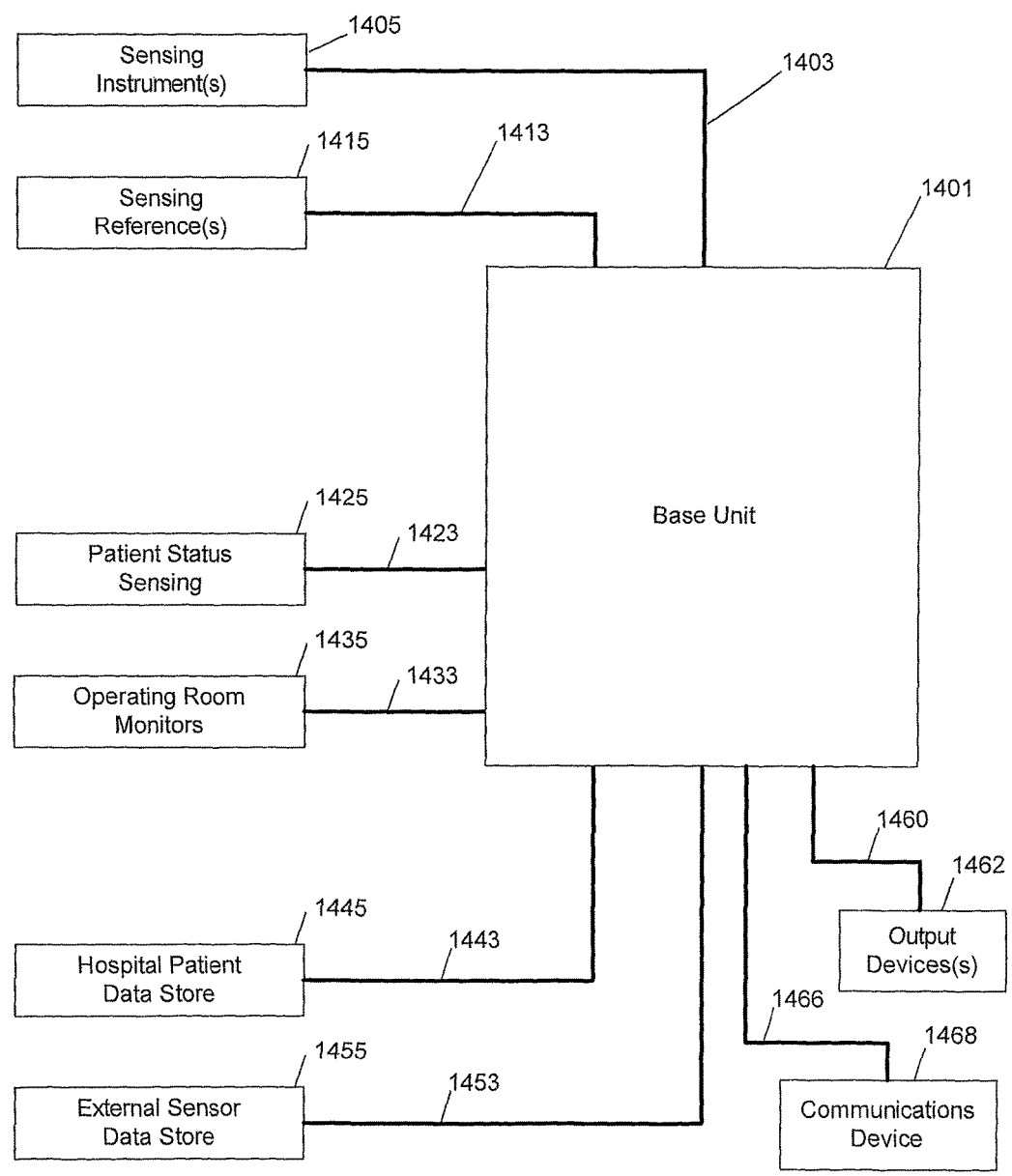
FIG. 14 is a block diagram of an intelligent expert system according to an embodiment of the present invention with integrated sensing, monitoring, data storage, outcome prediction, and display capabilities.

FIG. 14 shows a schematic layout of an integrated expert system according to the present invention. The base unit 1401 contains all processing, sensing, control, signal processing, communication, storage, and other required components. Coupled via coupler 1403 is sensing surgical instrument(s) 1405. These instruments include, but are not limited to, all of the instruments and embodiments described hereinabove. Sensing modalities include, but are not limited to, any of those described herein, including oxygenation including oximetry-type sensing, fluorescence, tissue perfusion, general health, tissue electrical impedance, tissue electrical activity, interaction forces, pH, electromyography, temperature, spectroscopy, fluid flow rate including laser or ultrasound Doppler measurement, fluid flow volume, pressure, levels of biomolecules and electrolytes, biomarkers, radiotracers, immunologic, chemical, nerve activity, evoked potential, and other sensor types capable of determining characteristics of tissue. Coupling 1403 is electrical, optical, and/or wireless. Instruments 1405 are tethered via electrical or optical cables, have built in wireless functionality, or have a reusable battery powered wireless pack that powers the instrument's sensors and/or the instrument itself, and/or couples the signals to the base unit 1401. A reference measurement sensor 1415 of the same type as said surgical instruments and coupled via coupler 1413 to base unit 1401 is used to obtain patient-specific reference measurements used to help determine tissue health and predict procedural outcomes. In addition to the instruments, a robotic manipulator useable to control the instruments and or reference sensor is coupled to the base unit 1401. The manipulator can be controlled in a closed loop fashion to optimize procedural outcomes responsive to real-time and prior patient specific information and prior statistical and other data.

Patient status sensing including cameras, infrared imaging, thermal imaging, spectroscopic imaging, and other sources 1425 and operating room monitors 1435 including anesthesia equipment monitors and vital signs monitors which include, but are not limited to, pulse rate and quality measurement, respiration rate and quality measurement, blood pressure measurement, blood gas analysis, pulse oximetry, and ECG, feed into base unit 1401 via couplings 1423 and 1433 respectively. This systemic data is recorded and synchronized with that of the sensing instruments, and also aids in determining tissue health and in predicting procedural outcomes. The system can also be coupled via coupling 1443 to the hospital's patient data storage system 1445 so that collected data is included in the database of patient medical history information. Further, patient medical history is incorporated into the system's analysis of sensor data to better predict and optimize outcomes.

All relevant data collected and post-procedural outcomes are stored in a central repository 1455 that is used to generate a statistical model that allows prediction of outcomes based on current sensor data. The coupling 1453 is bi-directional; prior data is used for analysis of the current procedure and current patient data and outcomes are added to the database 1455 for future use. Coupling 1453 need not be a permanent connection; data in a local copy of 1455 can be retrieved from and updated on each base unit 1401 at regular service intervals.

The collected data, statistical model, predicted outcomes, and other relevant information is presented in a comprehensible manner to the surgeon or other operating room staff using one or more output devices 1462 coupled to base unit 1401 via coupling 1460. Coupling 1460 is wired or wireless, or output device 1462 can be integrated directly into the control unit 1401. Presentation of results can be performed in numerous ways including, but not limited to: visual feedback, audio feedback, force or other haptic feedback, or other forms of sensory substitution. The feedback can include plots, text-based messages, verbal messages, audible warnings, video overlays, and feedback on a robotic manipulator. Communication with an external database or other source of data is achieved with a communication device 1468 communicatively coupled to the base unit 1401 via 1466. The coupling can be wired, wireless, or the communications device may be embedded in the base unit. Communications device 1468 can be a conventional modem, or an internet or other network connection.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only an exemplary embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A surgical instrument comprising:
    an optical emitter comprising first and second light sources respectively emitting different first and second spectrums of wavelengths onto the biological tissue, the first and second spectrums respectively including a broad spectrum of wavelengths and a spectrum centered at a predetermined wavelength;
    an optical filter comprising a band pass filter allowing light emitted by the biological tissue to pass;
    a first optical detector configured to detect light of the first broad spectrum of wavelengths emitted by the first light source that is reflected from the biological tissue, and a second optical detector configured to detect light emitted from the biological tissue in response to the light of the second spectrum centered at the predetermined wavelength emitted by the second light source and that is allowed to pass through the optical filter; and
    a processor configured to measure a parameter based on the light detected by the first and second optical detectors, and to measure a fluorescence response of light detected from the second optical detector when the second light source emits the second spectrum of wavelengths relative to a baseline response of light detected from the second optical detector when the second light source does not emit the second spectrum of wavelengths.

2. The surgical instrument of claim 1, wherein the processor is further configured to characterize tissue substructure based on the light detected by at least one of the first and second optical detectors and guide a current surgical procedure.

3. The surgical instrument of claim 2, wherein the processor is further configured to identify blood vessels based on the light detected by at least one of the first and second optical detectors.

4. The surgical instrument of claim 2, wherein the processor is configured to characterize tissue substructure including substructure of blood vessels or bile ducts.

5. The surgical instrument of claim 1, wherein the processor is further configured to identify regions of tissue with depleted blood supply based on the light detected by at least one of the first and second optical detectors.

6. The surgical instrument of claim 1, wherein the first and second optical detectors include a plurality of optical detectors disposed in a linear or grid like arrangement.

7. The surgical instrument of claim 6, wherein each optical detector disposed in the linear or grid like arrangement includes a respective photodiode, charge coupled device (CCD) sensor, complementary metal oxide semiconductor (CMOS) sensor, or spectrometer.

8. The surgical instrument of claim 1, wherein the first and second optical detectors include a plurality of optical detectors disposed in an array and operative to assess perfusion at discrete points, and the processor is configured to determine the presence of regions with variations in perfusion at the discrete points based on the light detected by the plurality of optical detectors.

9. The surgical instrument of claim 1, wherein the processor is configured to assess perfusion of the biological tissue based on the optical response of re-emitted light from an injectable probe, wherein the injectable probe is excited by the light emitted by the second light source and the re-emitted response is detected by the second optical detector.

10. The surgical instrument of claim 1, wherein the second optical detector is configured for fluorescence imaging of a light re-emitting medium perfused in the biological tissue.

11. The surgical instrument of claim 10, wherein the second optical detector is configured for fluorescence imaging of a fluorescent dye serving as the light re-emitting medium perfused in the biological tissue.

12. The surgical instrument of claim 1, wherein the first light source outputs white light.

13. A surgical system comprising:
the surgical instrument of claim 1; and
a robotic manipulator coupled to the surgical instrument and operative to control the surgical instrument.

14. A surgical system comprising:
the surgical instrument of claim 1; and
a robotic manipulator coupled to the surgical instrument and controlled based on feedback from the processor of the surgical instrument.

15. The surgical instrument of claim 1, wherein the second optical detector has a location known with respect to an imaging device configured to obtain a video signal showing the biological tissue, and the processor is configured to overlay measured perfusion on the video signal showing the biological tissue which is obtained by the imaging device.

16. The surgical instrument of claim 1, wherein the second optical detector is configured to detect light that is emitted from the biological tissue in response to a fluorescent medium being introduced into the biological tissue, and the processor is configured to monitor the onset of a fluorescence response, including measuring of at least one of a slope or rise time of a fluorescence response, based on the light detected by the second optical detector following a variation in an amount of the fluorescent medium introduced into the biological tissue.

* * * * *